United States Patent
Fisher et al.

(10) Patent No.: US 7,517,973 B2
(45) Date of Patent: Apr. 14, 2009

(54) ASTROCYTE MODULATED GENES AND USES THEREOF

(76) Inventors: Paul B Fisher, 15 Gordon Pl., Scarsdale, NY (US) 10583; Zhao-zhong Su, 705 W. 170th St., New York, NY (US) 10032; Dong-chul Kang, 1605-4, Gwanyang-dong, Dongan-gu (KR) 431-060

( * ) Notice: Subject to any disclaimer, the term of this patent is extended or adjusted under 35 U.S.C. 154(b) by 0 days.

(21) Appl. No.: 10/975,280

(22) Filed: Oct. 27, 2004

(65) Prior Publication Data

US 2005/0172343 A1    Aug. 4, 2005

Related U.S. Application Data

(63) Continuation of application No. PCT/US03/11887, filed on Apr. 17, 2003.

(60) Provisional application No. 60/452,629, filed on Mar. 6, 2003, provisional application No. 60/376,375, filed on Apr. 29, 2002.

(51) Int. Cl.
  *C12N 15/00*  (2006.01)
  *C07H 21/00*  (2006.01)
(52) U.S. Cl. .................. 536/23.5; 435/320.1
(58) Field of Classification Search .......... 435/4, 435/5, 6, 7.1, 41, 69.1, 320.1, 325, 455, 245, 435/366; 536/23.2, 235; 530/300, 350; 514/2
  See application file for complete search history.

(56) References Cited

U.S. PATENT DOCUMENTS 6,022,741 A * 2/2000 Ting et al. ................ 435/366
6,114,141 A * 9/2000 Dropulic et al. ........... 435/69.1
2002/0182191 A1* 12/2002 Xu et al. ................ 424/93.21

FOREIGN PATENT DOCUMENTS

WO    WO 03/077875    *    9/2003

OTHER PUBLICATIONS

GenBank AK000745, *Homo sapiens* cDNA FLJ20738 fis, clone HEP08257, first available on Feb. 22, 2000.*
Kang et al., "Cloning and characterization of HIV-1-inducible astrocyte elevated gene-1, AEG-1," Gene, vol. 353 No. 1, pp. 8-15 (Jun. 2005).*
Sequence search alignment, us-10-975-280-1.mg, pp. 15-16, result 8.*
Bowie et al., "Deciphering the Message in Protein Sequences: Tolerance to Amino Acid Substitutions," Science, vol. 247 No. 4948, pp. 1306-1310 (Mar. 1990).*
BLAST results, Sep. 27, 2006.*
GenBank AF100421. "*Rattus norvegicus* LYRIC mRNA, complete cds.," Aug. 8, 2001.*
BLAST alignment of nucleotides 220-1968 of SEQ ID No. 1 with AF100421, Dec. 21, 2007.*
Emdad et al., "Astrocyte Elevated Gene (AEG)-1: recent insights into a novel gene involved in tumor progression, metastasis and neurodegeneration," Pharmacology & Therapeutics, vol. 114 No. 2, pp. 155-170 (May 2007).*
Sutherland et al., "3D3/lyric: a novel transmembrane protein of the endoplasmic reticulum and nuclear envelope, which is also present in the nucleolus," Experimental Cell Research, vol. 294 No. 1, pp. 94-105 (Mar. 2004).*

* cited by examiner

*Primary Examiner*—Zachariah Lucas
(74) *Attorney, Agent, or Firm*—Baker Botts LLP

(57) ABSTRACT

The present invention relates to Astrocyte Enhanced Genes (AEGs), the expression of which is upregulated in human astrocytes grown in primary cell cultures that are exposed to either the human immunodeficiency virus (HIV-1) or to the HIV-1 glycoprotein gp120.

7 Claims, 21 Drawing Sheets

Figure 1:
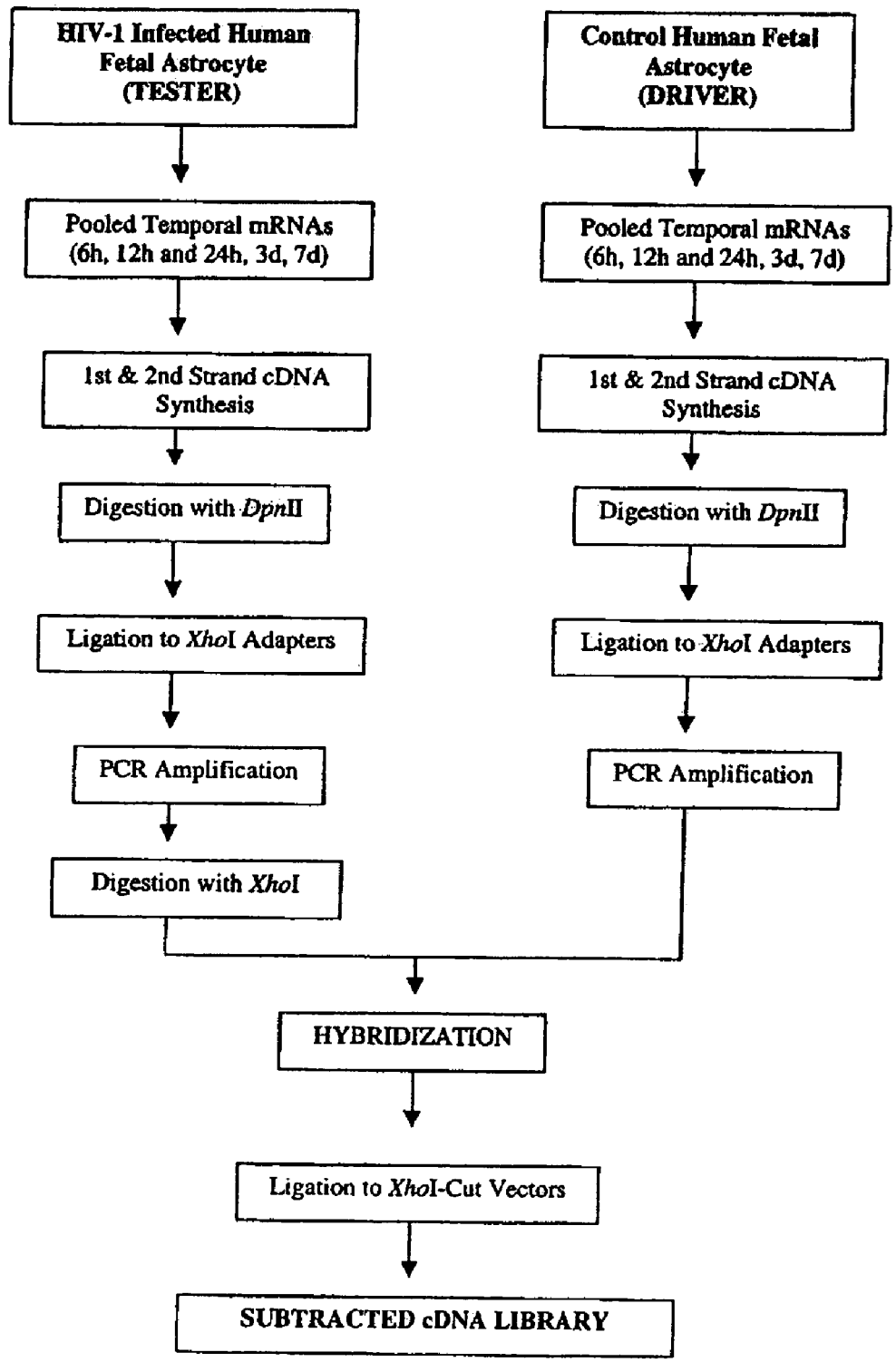

```
tcctggcggc ggcggagtga ggctgacagc ggggaacctg ggagacccct ccgccctccc    60
cgcggtggca gcggccgatc cccggctccg gcgcgaggga cggccgcgat gcgctcggcc   120
tgaggttacc cggcccggcc cttcctcgct tccctcgact attccactgc gtctccgcgc   180
cccggcgtca tcctgcgagt ccctctgacg ggagggaag atg gct gca cgg agc     234
tgg cag gac gag ctg gcc cag cag gcc gag gag ggc tcg gcc cgg ctg    282
cgg gaa atg ctc tcg gtc ggc cta ggc ttt ctg cgc acc gag ctg ggc    330
ctc gac ctg ggg ctg gag ccg aaa cgg tac ccc ggc tgg gtg atc ctg    378
gtg ggc act ggc gcg ctc ggg ctg ctg ctg ctg ttt ctg ctg ggc tac    426
ggc tgg gcc gcg gct tgc gcc ggc gcc cgc aaa aag cgg agg agc ccg    474
ccc cgc aag cgg gag gag gcg gcg gcc gtg ccg gcc gcg gcc ccc gac    522
gac ctg gcc ttg ctg aag aat ctc cgg agc gag gaa cag aag aag aag    570
aac cgg aag aaa ctg tcc gag aag ccc aaa cca aat ggg cgg act gtt    618
gaa gtg gct gag ggt gaa gct gtt cga aca cct caa agt gta aca gca    666
aag cag cca cca gag att gac aag aaa aat gaa aag tca aag aaa aat    714
aag aag aaa tca aag tca gat gct aaa gca gtg caa aac agt tca cgc    762
cat gat gga aag gaa gtt gat gaa gga gcc tgg gaa act aaa att agt    810
cac aga gag aaa cga cag cag cgt aaa cgt gat aag gtg ctg act gat    858
tct ggt tca ttg gat tca act atc cct ggg ata gaa aat acc atc aca    906
gtt acc acc gag caa ctt aca acc gca tca ttt cct gtt ggt tcc aag    954
aag aat aaa ggt gat tct cat cta aat gtt caa gtt agc aac ttt aaa   1002
tct gga aaa gga gat tct aca ctt cag gtt tct tca gga ttg aat gaa   1050
aac ctc act gtc aat gga gga ggc tgg aat gaa aag tct gta aaa ctc   1098
tcc tca cag atc agt gca ggt gag gag aag tgg aac tcc gtt tca cct   1146
gct tct gca gga aag agg aaa act gag cca tct gcc tgg agt caa gac   1194
act gga gat gct aat aca aat gga aaa gac tgg gga agg agt tgg agt   1242
gac cgt tca ata ttt tct ggc att ggg tct act gct gag cca gtt tct   1290
cag tct acc act tct gat tat cag tgg gat gtt agc cgt aat caa ccc   1338
tat atc gat gat gaa tgg tct ggg tta aat ggt ctg tct tct gct gat   1386
ccc aac tct gat tgg aat gca cca gca gaa gag tgg ggc aat tgg gta   1434
gac gaa gaa aga gct tca ctt cta aag tcc cag gaa cca att cct gat   1482
gat caa aag gtc tca gat gat gat aaa gaa aag gga gag gga gct ctt   1530
cca act ggg aaa tcc aaa aag aaa aag aaa aag aag aag caa ggt       1578
gaa gat aac tct act gca cag gac aca gaa gaa tta gaa aaa gag att   1626
aga gaa gac ctt cca gtg aat acc tct aaa acc cgt cca aaa cag gaa   1674
aaa gct ttt tcc ttg aag acc ata agc act agt gat cca gcc gaa gta   1722
ctc gtc aaa aat agc cag cct atc aag act ctt cca cct gct act tct   1770
acc gag cca tct gta atc tta tca aaa agt gat tct gac aag agc tct   1818
```

FIGURE 14

```
tcc caa gtg ccg cca ata cta caa gag aca gat aaa tcc aag tca aat    1866
acc aag caa aat agt gtg cct cct tca cag acc aag tct gaa act agc    1914
tgg gaa tct ccc aaa caa ata aaa aag aag aaa aaa gcc aga cga gaa    1962
acg tga aatttttttt cctgaattgg acatgtgttt gcaaacactt gtcttgaaga     2018
ttatgctgtt tatgcaataa tttgtgaaca tgtacagagt tttatataaa tttaaaccaa 2078
ttttttaaaac aaaactgcgg acaccaccat aaaaatggaa tcaaaagaaa gttaatttat 2138
gaaattaaga ggtcagcaga atatactcag tgatggaaga cacttgggaa agtcttttta 2198
atagaacaag aacgatctta atttaagaat attatcctgg tttaacaaca gtgccctgtt 2258
tacaacagat tgtgccctat ctcatctgca gccgaggaat aaaggattct gattagaaag 2318
agggttgcct acagattagt aagcaattcc ttggatctta tgcacagaac ttgtaccatt 2378
tgaatctgtt ttatgcttaa atcaaagtgc tttgatcaaa tgcataacct gccatatctt 2438
tacatatttg ttggtagcaa tttgtattaa agaaatcaca agtgcaaata aaaagtcatt 2498
tatcatttgt ttaactaaac tgtcatggtt tagtttacaa ttttttaaaaa gttcttaaaa 2558
tactgaaaat gcagttgaca cttgtgtatg gcttatgaag ttatttttga tagtcttaca 2618
ttacttgaat tgttcaaagt acagtatatt ttaaattaag aaaagtgaac tatatgtatt 2678
tgttttatac atttaaggct tagactcata aataatgcta ttgtttatga tttgaaaact 2738
ttcaggcaaa atccaattta cattttttccc ttccctagca attactttt tccagcttca 2798
actcttctta gttactaata ctttgttgac tttaaaaatg aaatcattca caaactttttg 2858
gtatatgatg gagaatgaaa aactagagtc agacagcttt aattgacatt gtcaacacct 2918
ccagttatca ggaatacatt ttttttactgc cttaacctgt agtgcgtaga atatgcatca 2978
atttcttgaa ggagattcat gtttttataa gaatttttcat gtaattattg caattgtggt 3038
caaataagga acgttcctg cttgaaatta tattgattta aatgatgtgt gagatgtttc 3098
accatttttca ggcactgtgt aattctattg taataaactg gcaggtatct ttgtaactat 3158
aaatagtgca tgctcagcca tgtacactgt aaatagcctt taccaaacgt gtttgacaag 3218
gaccataatt aacatcactt agtgaattgt gataaagaaa aaaaagccat gatttattcg 3278
atgtgattgg cttgttttta tgtggcgcca agaacgaacc tgtttaacag ctgtaaccaa 3338
tggtactgat ctatccatcc aatgttgtca ttatatttga ctgtggttca acagtattgc 3398
gttgtcagac taggaaagct aaacgaacaa aatggtttta gttttgctga agactggcct 3458
tattaatgga cagctttcct aacaagagat tattaacttt tatcaggtgt taacatctgt 3518
ttcaggaaca tggcagtatg tttacatgtc agaagttttg tttaattcta tggtatttct 3578
aaattgactt gtttaaataa attcagcaaa tgg                               3611
```

FIGURE 14 (CONT'D)

```
Met Ala Ala Arg Ser Trp Gln Asp Glu Leu Ala Gln Gln Ala Glu Glu
 1               5                      10                  15
Gly Ser Ala Arg Leu Arg Glu Met Leu Ser Val Gly Leu Gly Phe Leu
             20              25                  30
Arg Thr Glu Leu Gly Leu Asp Leu Gly Leu Glu Pro Lys Arg Tyr Pro
         35              40              45
Gly Trp Val Ile Leu Val Gly Thr Gly Ala Leu Gly Leu Leu Leu Leu
 50                  55                  60
Phe Leu Leu Gly Tyr Gly Trp Ala Ala Ala Cys Ala Gly Ala Arg Lys
 65              70                  75                      80
Lys Arg Arg Ser Pro Pro Arg Lys Arg Glu Glu Ala Ala Ala Val Pro
             85              90                      95
Ala Ala Ala Pro Asp Asp Leu Ala Leu Leu Lys Asn Leu Arg Ser Glu
             100             105                 110
Glu Gln Lys Lys Lys Asn Arg Lys Lys Leu Ser Glu Lys Pro Lys Pro
         115             120                 125
Asn Gly Arg Thr Val Glu Val Ala Glu Gly Glu Ala Val Arg Thr Pro
         130             135             140
Gln Ser Val Thr Ala Lys Gln Pro Pro Glu Ile Asp Lys Lys Asn Glu
 145             150                 155                     160
Lys Ser Lys Lys Asn Lys Lys Lys Ser Lys Ser Asp Ala Lys Ala Val
             165             170                 175
Gln Asn Ser Ser Arg His Asp Gly Lys Glu Val Asp Glu Gly Ala Trp
             180             185                 190
Glu Thr Lys Ile Ser His Arg Glu Lys Arg Gln Gln Arg Lys Arg Asp
         195             200                 205
Lys Val Leu Thr Asp Ser Gly Ser Leu Asp Ser Thr Ile Pro Gly Ile
         210             215             220
Glu Asn Thr Ile Thr Val Thr Thr Glu Gln Leu Thr Thr Ala Ser Phe
 225             230             235                     240
Pro Val Gly Ser Lys Lys Asn Lys Gly Asp Ser His Leu Asn Val Gln
             245             250                 255
Val Ser Asn Phe Lys Ser Gly Lys Gly Asp Ser Thr Leu Gln Val Ser
             260             265                 270
Ser Gly Leu Asn Glu Asn Leu Thr Val Asn Gly Gly Trp Asn Glu
         275             280             285
Lys Ser Val Lys Leu Ser Ser Gln Ile Ser Ala Gly Glu Glu Lys Trp
         290             295             300
Asn Ser Val Ser Pro Ala Ser Ala Gly Lys Arg Lys Thr Glu Pro Ser
 305             310             315                     320
Ala Trp Ser Gln Asp Thr Gly Asp Ala Asn Thr Asn Gly Lys Asp Trp
             325             330             335
Gly Arg Ser Trp Ser Asp Arg Ser Ile Phe Ser Gly Ile Gly Ser Thr
         340             345             350
Ala Glu Pro Val Ser Gln Ser Thr Thr Ser Asp Tyr Gln Trp Asp Val
         355             360             365
Ser Arg Asn Gln Pro Tyr Ile Asp Asp Glu Trp Ser Gly Leu Asn Gly
         370             375             380
Leu Ser Ser Ala Asp Pro Asn Ser Asp Trp Asn Ala Pro Ala Glu Glu
 385             390             395                     400
```

FIGURE 15

```
Trp Gly Asn Trp Val Asp Glu Glu Arg Ala Ser Leu Leu Lys Ser Gln
                405                 410                 415
Glu Pro Ile Pro Asp Asp Gln Lys Val Ser Asp Asp Lys Glu Lys
            420                 425             430
Gly Glu Gly Ala Leu Pro Thr Gly Lys Ser Lys Lys Lys Lys Lys
        435                 440             445
Lys Lys Lys Gln Gly Glu Asp Asn Ser Thr Ala Gln Asp Thr Glu Glu
    450                 455                 460
Leu Glu Lys Glu Ile Arg Glu Asp Leu Pro Val Asn Thr Ser Lys Thr
465                 470                 475                 480
Arg Pro Lys Gln Glu Lys Ala Phe Ser Leu Lys Thr Ile Ser Thr Ser
            485                 490                 495
Asp Pro Ala Glu Val Leu Val Lys Asn Ser Gln Pro Ile Lys Thr Leu
            500                 505                 510
Pro Pro Ala Thr Ser Thr Glu Pro Ser Val Ile Leu Ser Lys Ser Asp
            515                 520                 525
Ser Asp Lys Ser Ser Ser Gln Val Pro Pro Ile Leu Gln Glu Thr Asp
    530                 535                 540
Lys Ser Lys Ser Asn Thr Lys Gln Asn Ser Val Pro Pro Ser Gln Thr
545                 550                 555                 560
Lys Ser Glu Thr Ser Trp Glu Ser Pro Lys Gln Ile Lys Lys Lys Lys
            565                 570                 575
Lys Ala Arg Arg Glu Thr
            580
```

FIGURE 15 (CONT'D)

```
GCGGAAATAA ACAAAATGAG TAGACATGGG AACATAAAAT ACATTGTGGA
ATATCCAAGT AATAATGCAT TATGACATTA TCTAATGTTT CTGAAGAACA
TATATTATCA AGGGNAATGG CCGCATTCTT TTCATGCCCA TGGCAGACAG
AGCAAACCTA AATGTGCAAG CATATATCAA GCTTCTGTAG AGTCAGGTTT
CTCAAATTAT CATTGACCAA AATAAGTTAC ATGGCCAAGG CCAAGCTCTA
CATCAATAAT CAGGAAACAG CTGGGTGCAG TGGCTCACAC TATTTTCATA
TTATTAGTAT TAAAATTCCC ATTTGCATAT GGTTATAGAT TTCTTACCAA
CTTCCATATT TTCAAACTGA AAAAATGTAA AACTAAATTC TTTTTTAGAA
ACTCCATGTG TGATAAATAA AATTATTTAA CATTTTGGTG TAATATTTAC
AAATCCTGCA AAATAGCACC CAGATCCTTG GTTGATGCCA GAGTCACTCT
GCATTATGCA ATGACACTTT AGGCAAAAG TAATAATAAT AGCTGCAAAG
AAACATTCAA GAATACTGTA CTAAATGCAA CTAAACTCTA CAATAAATGC
AAAGTATCAG CACTTAAGTG GATTAGTTGA AGTGTGCCAT TATCATGCCA
GGGTGACATA ACACAACACA ATGGCATATA CCATTGTATC AGAGTAGAGG
AAACCTTTCT CTCCTTTTCA CATTTGCATA TGGTTACGTT TAAATTACCA
CCTATTTTAT ATAATAACTG GCAGGTGTTA TGATAAAGAT ATTAAATAAC
ATTCCATTTT TTCATTAAAG AAATCAAAAT ATAGAATAGC CCTAAAGAAA
CTGAGAGTTG TGTACAGGTT TTATGAGCAC AGAAGCACTT TTAAATATGT
AACAGGGGAC ATGCAAACAT TGGAACATCA GAATTAGCCA CCGTAATTCT
CTAATCTCCA TGTTTCTATT TGTATATAAT CTGAAACAGG GAAACTATAC
TCACAATCAG GGAAAACTAC TGGTAAATTG TTCATGCCAT TGCATAATAA
AATGGCTAAA GTAGTTAAAA AGTAATGAAT CTGGAAGTCT TTAGCAGACA
TATTCAGTGT AACTTATGTC ACACTTAAAA GAGAAAATA GTATTAAAAA
TTAGAGATCT TTTATCTTCC CTTAGTAAAT AACCTTTTCT ATCGAAACAA
AATTACTTGA GTCTAAATCC TGTTATAAGC ACAGTGTTAG ATATCTTACA
TATATTATTT CATTGAATAC TAACAAAAAA CCCTTTGATA AACATGGTAT
TCTTCCCAGT TTATAGAGAT GGAAACATAG AAATTAGGTA ATGTGCCCAT
GTTTGTACAG GTAATAAGTG GTAGACCTGG ATCTAAAATA CATATTAGGC
TTCAAACTAA TTCATACTCT AAAAGAATAT TTGCCAAAGT ACATAATACA
ATTTGCTAAC AGATGCTAAG GTAAACAAAA AATTGATTAT GATAGTTAAT
TTACACAAGG ATAAGTTATA AGCTAAAATA TTTTTTTCCC TTAACAAAAT
ATTATGTATC ATTTATTTAT TTATTTTTTT GAAACGGAGT CTCG
```

FIGURE 16

```
gagagctctc attttccccc cttgctcggg atggtgccac aggaggctgt
gcgggccccg ctccgcttcg aatggttgtg ttgatgttcc tttcagctgg
tcctatagta cccctcctca ggaatgtctc cccagtgcaa ggacaaagac
tgaagagact gctatattga tggactctca agccaactat gaagttgaaa
caaagaaagt gatcacctga agacacctcc tctgctaaga aacacccca
aattgtgcag cttctgccac tagaactctc agaacaagag acaatctttt
caagaaacag aaaaactcaa taatgacatc tagattttca tgagccaaga
actttccctt cctcatgtgt attcctctgt ttgtacttaa attcatgtga
cattcatttt tttcctagta tggatatgct tattaatgca cttgtttcaa
aatcccaaat tgcacaaatg tgttaatatt ttaagaaaca aaatgaatcc
tacaaggaga atgattttta gccacacata gggttggatc ttgagagtga
cctacagaat aaaagtactt ttaaaataaa gtagtcagag gctattcaaa
gggtaaaata atcatagtac cacattggtc cacttgacac taaccaatcg
atcatttttt tttaatcaag aaagctagat tctatcagat aaaatcactg
cttctaaaga gtttaaatct agttagaaaa agttatagaa atgtttgcaa
agataagtaa cagatagagt cagtagagga taagatcaaa aacaaaacca
agcaaaagat gagttcaggg gagtttgcca tcaagttggc aaaactgact
tacttaggga agaaagttat aaaacaggaa aatatgagat gaaccttgag
tgatgtggaa gatttagata aatggaaagg aaggagaaaa tggagttctt
taggtggttg taattggagg aggaaatgaa tacacacatc ttgttgactt
aaacccagac attcagcagc tctctataca tatctggaaa agactgcaca
gtcacctcct gtctctcacc ccaggtatta cttagaatta ttatcatatt
tcccttcctt taaagtaagt aagggtgatt ggtgacaata tggagaacta
tgattttttcc attaacctaa taataattgg tatttattga gttctgttaa
gcattttaca tattaactca cttaagcctt tcaacagcct tgcaaaatag
gtattattat ccccatttta caggcaagaa aactgaggtt taagtaactt
gccgaagtgc catatacagg gctcacattc agtattgcag ttgcaaagct
catgatctat agtgccaagt tgcaatattg tagtcaatgt cacaattatt
accccttttt atattccttg atattttcc atggcaaaca attagctatt
tcatttaata atcacctaaa actttttcagt cttctgatta aaattacgct
ggagtgatag aatgtatttt catgatagaa attgggaaaa aaaatgggga
atgaagttta tcagcatttc agcttgtttt ttttttttt ttttttgcaa
gactttgatg agattgttca cttttgtcta tgtaaaatcc caaatccttg
agaataaaaa aggggggaggt ttaagtcact tgttgcaatg ccctttttaa
tagaggcaat aaatctaaag gccataaatt tagagtgact tacagaagat
cgaactttgg agtgtggcag agtaagggat ggaaccggg ccctccagtt
cactatcagt agcttttgca ctggtctgcc ttcctaaat taagtatgca
cttcaatttg atgagtggaa acagtctatc tgggcagtaa ccagggagct
ttgtgcctag tagattgctt ctgttctgca cttctttggt ttcccacctc
```

FIGURE 17

```
aatgtaaaaa atagctagca atgaagtcca gaagttgtca atggttcatc
cccagaagaa tgcataatgt ccaaagttgt atgtgtatga tgtcttcaat
ggtattaagt tatttcaaat tcttagttca cctacataaa tcatttctaa
caagcatctt cttaaccaac tttatgcaca gtgtatgttt gtaagtgctt
ctgcacgaat gtttatacat gactgtttcc atagtactta tgttttttaaa
aatattcagt catttcctac tataatcctc atgtatccat gtaactgact
caaaaatact tcagccacag aaagctaaaa ctgagcaaat ctcattcttc
ttttccatcc cctttgcatg tggctggcat ttagtaatga ttaataatat
ggccagctga ataacagagg tttgagacac aattctttct caaaggagtc
agctaagctg ggtctactta tggacaaaca tctaaatgtg tggaagtatc
tgatatttga caatggtaaa tttccactta gctagctagc attgtcagac
ttcaatctcc tcatggctct ggccgtcctg ttttaagcat gataattgtt
ggccacatct cacatagttc tcattgagtg agttcataaa taaacagggt
tttttttttt tttaaagagc agccaagcac aaagtgtgac tttgttgaca
ttttatgtga ctttgtcata tgttcctaac ccccaataaa agcaatgttg
caccaaaaaa aaaaaaaaaa
```

FIGURE 17 (CONT'D)

ASTROCYTE MODULATED GENES AND USES THEREOF

This application is a continuation of International Patent Application No. PCT/US2003/011887 filed Apr. 17, 2003 and published as WO 2004/016732, which claims priority to Provisional U.S. Patent Application No. 60/376,375 filed Apr. 29, 2002 and Provisional U.S. Patent Application No. 60/452,629 filed Mar. 6, 2003, incorporated by reference in their entireties herein.

The subject matter described herein was supported in part by National Institutes of Health Grant 5P01NS031492, so that the United States Government has certain rights herein.

1. INTRODUCTION

The present invention relates to Astrocyte Modulated Genes (AMGs). AMGs are genes whose expressions are modulated in human astrocytes grown in primary cell culture and exposed to either the human immunodeficiency virus HIV-1 or to the HIV-1 protein gp120. AMGs comprise Astrocyte Enhanced Genes (AEGs) and Astrocyte Suppressed Genes (ASGs) among those astrocyte genes whose expression patterns are altered following exposure to HIV-1 or gp120. Because they may play a role in HIV-associated dementia ("HAD"), AMGs may be used as markers in methods for screening for drugs that treat or prevent HAD.

2. BACKGROUND OF THE INVENTION

Glial cells are the predominant cell type in the brain, constituting more than 50% of the total cell count and outnumbering neurons 10-fold (Schubert, 1984, *Developmental Biology of Cultured Nerve, Muscle, and Glia*. Wiley and Sons, New York; Rutka et al., 1997, *J. Neurosurg.* 87, 420-430). Two major subtypes of glia are distinguished by their distinct functions in the nervous system: oligodendrocytes, which form myelin sheaths around nerve cell axons, and astrocytes, which maintain brain homeostasis and respond to pathogens and brain injury (Benveniste, 1992, *Am. J. Physiol.* 263, C1-16; Verkhratsky et al., 1998, *Physiol. Rev.* 78, 100-130).

Historically, astrocytes were considered to provide mostly passive support to neurons and the overall function of the nervous system. Recent studies question this hypothesis and suggest that astrocytes also play a critical role in several aspects of signal transmission and that defects in these functions may lead to neurodegeneration (Choi, 1988; *Neuron* 1, 623-634; Rothstein et al., 1996, *Neuron* 16, 675-686; Verkhratsky et al., 1998, *Physiol. Rev.* 78, 100-130; Anderson & Swanson, 2000, *Glia* 32, 1-14). For example, the high-affinity excitatory amino acid transport systems acting through astrocyte-specific transporters EAAT1 and EAAT2 are thought to be primarily responsible for maintenance of low levels of free intrasynaptic L-glutamate, the major excitatory neurotransmitter in the brain (Choi, 1988; *Neuron* 1, 623-634; Benveniste, 1992, *Am. J. Physiol.* 263, C1-16; Anderson & Swanson, 2000, *Glia* 32, 1-14). Defects that specifically abrogate this function result in accumulation of extracellular glutamate in synaptic clefts and overexcitation and death of neurons, a phenomenon referred to as excitotoxicity (Choi, 1988; *Neuron* 1, 623-634; Gegelashvili, G. & Schousboe, A. (1997). *Molec. Pharmacol.*, 52, 6-15; Tanaka et al., 1997, *Science* 276, 1699-1702).

At least one neurodegenerative disease, Amyotropic Lateral Sclerosis (ALS), has been linked to a significant decrease of high-affinity sodium-dependent glutamate transport in synaptic membranes (Rothstein et al., 1992, *New Engl. J. Med.* 326, 1464-1468) and a selective loss of the transporter EAAT2 (Bristol & Rothstein, 1996, *Ann. Neurol.* 39, 676-679). Similar defects are implicated in Alzheimer's disease, stroke/ischemia, epilepsy, and HIV-1-associated dementia (HAD) (Choi, 1988, *Neuron* 1, 623-634; Kaul et al., 2001, *Nature* 410, 988-994; Maragakis & Rothstein, 2001, *Arch. Neurol.*, 58, 365-370).

In addition to their role in glutamate removal from synapses, astrocytes significantly increase the number of synapses and enhance synaptic efficacy by altering pre- and post-synaptic functions in vitro (Oliet et al., 2001, *Science* 292, 923-926; Ullian et al., 2001, *Science* 291, 657-660). Finally, astrocytes appear to share many properties with neurons, including expression of functional neuronal nicotinic acetylcholine receptors (nACHRs) and competence for $Ca^{++}$-dependent glutamate release, thus permitting intercellular signaling between astrocytes and neurons and, possibly, modulation of neuronal signal transmission by astrocytes (Iino et al., 2001, *Science* 292, 926-929; Sharma & Vijayaraghavan, 2001, *Proc Natl Acad Sci USA* 98, 4148-4153; Ullian et al., 2001, *Science* 291, 657-660).

Overall, these studies suggest that astrocytes and neurons are functionally integrated and that pathogenic stimuli that adversely affect astrocytes will directly or indirectly impact on neuronal function and survival.

Studies have focused on investigation of HIV-1 infection in neural cells and the potential contribution of such infections to neurodegeneration and HAD. The pathogenic events triggered by HIV-1 in the brain, which ultimately result in neuronal loss and CNS dysfunction (Navia et al., 1986a, *Ann. Neurol.* 19, 525-535; Navia et al., 1986, *Ann. Neurol.* 19, 517-524; reviewed in Lipton & Gendelman, 1995, *New Engl. J. Med.* 233, 934-940), have not been fully resolved. Neurons are rarely infected in vivo (Wiley et al., 1986, *Proc. Natl. Acad. Sci. USA* 83, 7089-93) and it is unlikely that neuronal loss in HIV-1 dementia is caused by cytopathic infection of these cells.

Numerous neuropathology, immunocytochemistry, in situ hybridization, and virus isolation studies indicate that macrophages and microglial cells are the primary host cells for productive HIV-1 infection in the CNS (Koening et al., 1986, *Science* 233, 1089-1093; Brew et al., 1995, *Ann. Neurol.* 38, 563-570; reviewed in Lipton & Gendelman, 1995, *New Engl. J. Med.* 233, 934-940). It has been suggested that HV-1 infection and subsequent activation of infected cells causes neuroinflammatory responses involving production of chemokines, cytokines, nitric oxide, and other factors, some of which were shown to be neurotoxic in vitro (reviewed in Lipton & Gendelman, 1995, *New Engl. J. Med.* 233, 934-940; Kaul et al., 2001, *Nature* 410, 988-994). Viral products secreted by infected cells, including gp120 and Tat, can also induce neurotoxicity in vitro and in animal models (Lipton & Gendelman, 1995, *New Engl. J. Med.* 233, 934-940; Kaul et al., 2001, *Nature* 410, 988-994).

Astrocytes also can be infected with HIV-1 in vitro and in vivo, although with lower efficiency than T cells and macrophages (Dewhurst et al., 1987, *J. Virol.* 61, 3774-3782, *J. Virol.* 61, 3774-3782; Tomatore et al., 1991, *J. Virol.* 65, 6094-6100; Saito et al., 1994, *Neurology* 44, 474-481; Tomatore et al., 1994, *Neurology* 44, 481-487; reviewed in Brack-Wemer, 1999, *AIDS* 13, 1-22). The limited infection of astrocytes has been attributed to various mechanisms including intracellular restrictions to virus expression (Tomatore et al., 1994b, *J. Virol.* 68, 93-102; Gorry et al., 1999, *J. Virol.* 73, 352-61; Ludwig et al., 1999, *J. Virol.* 73, 8279-8289) or, as has been shown recently, inefficient virus entry (Bencheikh et al., 1999, *J. Neurovirol.* 5, 115-124; Canki et al., 2001, *J.*

Virol. 75, 7925-7933). There is general agreement, however, that HIV-1 can persist in astrocytes for prolonged periods in a low productive, non-cytolytic state, from which it can be induced by physiologic stimuli such as tumor necrosis factor-α (TNF-α) (Tornatore et al., 1991, *J. Virol.* 65, 6094-6100; Shahabuddin et al., 1992, *Pathobiology* 60, 195-205).

Surveys of autopsy tissues using in situ PCR and sensitive immunocytochemistry techniques indicate that the frequency of HIV-1-positive astrocytes in selected tissue sections from brains of patients with dementia can achieve 1% (Saito et al., 1994, *Neurology* 44, 474-481; Tomatore et al., 1994a, *Neurology* 44, 481-487; Takahashi et al., 1996, *Ann. Neurol.* 39, 705-711). Considering that the number of astrocytes in the brain is between $10^{11}$ to $10^{12}$ cells (Verkhratsky et al., 1998, *Physiol. Rev.* 78, 100-130), these cells clearly constitute a major target for HIV-1 infection in the brain.

The consequences of this infection with respect to HAD pathogenesis are unknown but they may be significant. Persistent, non-cytolytic HIV-1 infection in culture alters gene expression in lymphocytes (Shahabuddin et al., 1994, *AIDS Res. Hum. Retroviruses* 10, 1525-1529; Geiss et al., 2000, *Virology* 266, 8-16) and astrocytes (Schneider-Schaulies et al., 1992, *Virology* 191, 765-772; He et al., 1997, *Proc. Natl. Acad. Sci. USA* 94, 3954-3959), indicating that such infections may affect cell function. Exposure of astrocytes to recombinant HIV-1 envelope glycoprotein gp120 alters cell physiology (Benos et al., 1994a, *Adv. Neuroimmunol.* 4, 175-179), including a potential effect on glutamate transport as indicated by increased D-aspartate efflux in astrocytes treated with gp120 (Benos et al., 1994b, *Proc. Natl. Acad. Sci. USA* 91, 494-498). Impairment of glutamate transport was also observed after incubation of human astrocytes with TNF-α (Fine et al., 1996, *J. Biol. Chem.* 271, 15303-15306) or co-cultivation with T cells infected with human T cell leukemia virus type I (HTLVI) (Szymocha et al., 2000, *J. Virol.* 74, 6433-6441), and similar defects were found in feline astrocytes after infection with feline immunodeficiency virus (FIV) (Yu et al., 1998, *Proc. Natl. Acad. Sci. USA* 95, 2624-2629).

More recent studies indicate that ligation of the HIV-1 coreceptor on astrocytes, CXCR4, by either stromal cell-derived factor 1 (SDF-1) or gp120 can stimulate a novel signaling pathway that involves $Ca^{2+}$-dependent release of glutamate (Sharma & Vijayaraghavan, 2001, *Proc Natl Acad Sci USA* 98, 4148-4153) in a process including activation of the CXCR4 receptor, an autocrine/paracrine TNF-α-dependent signaling, and prostaglandin (Bezzi et al., 2001, *Nat. Neurosci.* 4, 702-710). These results suggest that HIV-1, gp 120, and other neuropathogenic agents can alter specific signaling pathways in astrocytes in a way that may impair important physiological functions of these cells in neuronal signal transmission and response to brain injury.

3. SUMMARY OF THE INVENTION

The present invention relates to Astrocyte Modulated Genes (AMGs). AMGs are genes whose expressions are modulated in human astrocytes grown in primary cell culture following the exposure of these cells to either the human immunodeficiency virus HIV-1 or to the HIV-1 protein gp120. AMGs comprise Astrocyte Enhanced Genes (AEGs) and Astrocyte Suppressed Genes (ASGs).

The invention is based, at least in part, on the results of a series of experiments in which a rapid subtraction hybridization (RaSH) method (Jiang et al., 2000, *Proc. Natl. Acad. Sci. USA* 97, 12684-12689) was used to globally identify human genes whose expression in astrocytes display temporal alterations following HIV-1 infection. Using this methodology, it was discovered that 15 AEGs, including 13 known and 2 novel genes, and 10 ASGs, including 9 known and 1 novel gene, displayed altered levels of expression in early passage human fetal astrocytes as a consequence of HIV-1 infection or treatment with gp120. These AMGs may be used as markers of HIV infection and/or pathology, and, as such, may be used as reporter genes in screening assays for identifying agents that inhibit or prevent such infection and/or pathology.

The invention is further based on the discovery that upregulation of one particular AMG, termed AEG-1, results in the downregulation of GLT-1, thereby increasing extracellular levels of the potentially excitotoxic neurotransmitter L-glutamate. In various embodiments of the invention, inhibition of AEG-1 may be used to facilitate glutamate transport and thereby prevent or decrease its toxic effects. As AEG-1 is constitutively present in astrocytes, inhibition of AEG-1 may be useful in preventing or decreasing glutamate toxicity in a variety of contexts, not limited to HIV infection, but including other pathologies as well, such as cerebral infarction and/or ischemia, Alzheimer's Disease, epilepsy, and amyotrophic lateral sclerosis. AEG-1 may be inhibited, for example, by antisense molecules or antagonists directed at the expressed protein. Such antagonists may be identified using screening assays which monitor AEG-1 levels, GLT-1 levels, and/or glutamate transport capability.

3.1. Definitions

As used herein, the term "nucleic acid molecule" includes both DNA and RNA and, unless otherwise specified, includes both double-stranded and single-stranded nucleic acids. Also included are molecules comprising both DNA and RNA, either DNA/RNA heteroduplexes, also known as DNA/RNA hybrids, or chimeric molecules containing both DNA and RNA in the same strand. Reference to a nucleic acid sequence can also include modified bases as long as the modification does not significantly interfere either with binding of a ligand such as a protein by the nucleic acid or Watson-Crick base pairing between two complementary nucleic acid molecules.

As used herein, the term "gene" refers to a DNA molecule that either directly or indirectly encodes a nucleic acid or protein product that has a defined biological activity.

As used herein, a specific, non-limiting example of stringent conditions for detecting hybridization of nucleic acid molecules are as set forth in "*Current Protocols in Molecular Biology*", Volume I. Ausubel et al., eds. John Wiley:New York N.Y., pp. 2.10.1-2.10.16, first published in 1989 but with annual updating, wherein maximum hybridization specificity for DNA samples immobilized on nitrocellulose filters may be achieved through the use of repeated washings of a hybridized filter in a solution comprising 0.1-2×SSC (15-30 mM NaCl, 1.5-3 mM sodium citrate, pH 7.0) and 0.1% SDS (sodium dodecylsulfate) at temperatures of 65-68° C. or greater. For DNA samples immobilized on nylon filters, a stringent hybridization washing solution may be comprised of 40 mM $NaPO_4$, pH 7.2, 1-2% SDS and 1 mM EDTA. Again, a washing temperature of at least 65-68° C. is recommended, but the optimal temperature required for a truly stringent wash will depend on the length of the nucleic acid probe, its GC content, the concentration of monovalent cations and the percentage of formamide, if any, that was contained in the hybridization solution. Stringent hybridizations are designed to identify molecules with 80% identity or preferably 90% identity or more preferably 95% identity over lengths of at least 15 nucleotides and preferably at least 50 nucleotides.

An Astrocyte Modulated Gene, or "AMG", as the term is used herein, is a gene the expression of which is modified in astrocytes as a result of HIV-1 infection and/or exposure to HIV-1 gp120 protein. AMGs comprise Astrocyte Enhanced Genes (AEGs), whose expression levels are upregulated following exposure of cultured human fetal astrocytes to HIV-1 and/or to the HIV-1 gp 120 protein, and Astrocyte Suppressed Genes (ASGs), whose expression levels are down-regulated following exposure of cultured human fetal astrocytes to HIV-1 and/or to the HIV-1 gp 120 protein. AMGs also comprise genes whose pattern of expression, e.g. the timing of expression, is changed following exposure of cultured human fetal astrocytes to HIV-1 and/or to the HIV-1 gp 120 protein. Increased expression is associated with higher levels of MRNA and/or protein, while reduced expression is associated with lower levels of MRNA and/or protein.

Examples of AEGs include: AEG-2 (G-binding protein), AEG-3 (GA17 protein) (Ryo et al., 2000, *AIDS Res. Hum. Retroviruses* 16, 995-1005), AEG-4 (unr/NRU) (Jeffers et al., 1990, *Nucl. Acids. Res.* 18, 4891-4899; Boussadia et al., 1993, *Biochim. Biophys. Acta* 1172, 64-72), AEG-5 (hGNT-IV-H) (Furukawa et al., 1999, *J. Hum. Genet.* 44, 397-401), AEG-6 (fibronectin), AEG-7 (human CTL2) (O'Regan et al., 2000, *Proc. Natl. Acad. Sci. USA* 97, 1835-1840), AEG-8 (acidic ribosomal phosphoprotein) (Rich & Stietz, 1987, *Mol. Cell. Biol.* 7, 4065-4074), AEG-9 (calnexin) (Honore et al., 1994, *Electrophoresis* 15, 482-490; Rubio & Wenthold, 1999, *J. Neurochem.* 73, 942-948; Shi et al., 2001, *Cell* 105, 331-342), AEG-10 (autotaxin) (Stracke et al., 1994, *J. Biol. Chem.* 267, 2524-2529; Kawagoe et al., 1997, *Cancer Res.* 57, 2516-25), AEG-12 (thymosin β-4) (Gondo et al., 1987, *J. Immunol.* 139, 3840-3848), AEG-13 (human non-muscle α-actinin) (Youssoufian et al., 1990, *Am. J. Hum. Genet.* 47, 62-72), AEG-14 (Schneider et al., 1988, *Cell* 54, 787-793; Gonos, 1998, *Ann. N.Y. Acad. Sci.* 851, 466-469; Prieto et al., 1999, *Brain Res.* 816, 646-661) and AEG-15 (PGK-1) (Michelson et al., 1983, *Proc. Natl. Acad. Sci. USA* 80, 472-476; Tsukada et al., 1991, *J. Gerontol.* 46, B213-B216), and the novel AEGs AEG-1 and AEG-11.

Examples of ASGs include: ASG-2 (human cDNA FLJ10705; GenBank Acc. No. AK001567, ASG-3 (Platelet-endothelial cell tetra-span antigen 3; CD151/PETA-3; Fitter et al., 1995, *Blood* 86, 1348-55; Yáñez-Mó et al., 1998, *J. Cell Biol.* 141, 791-804), ASG-4 (guanine nucleotide-releasing factor; C3G; Schweighoffer et al., 1993, *Oncogene* 8, 1477-85; Tanaka et al., 1994, *Proc. Natl. Acad. Sci. USA* 91, 3443-3447), ASG-5 (neuronatin; ASG-5; Dou & Joseph, 1996, *Brain Res.* 723, 8-22; Usui et al., 1997, *J. Mol. Neurosci.* 9, 55-60), ASG-6 (neuroendocrine differentiation factor; CGI149; Wilson et al., 2001, *J. Clin. Endocrinol. Metab.* 86, 4504-11), ASG-7 (cysteine/glycine-rich protein 1; CSRP1; Liebhaber et al. 1990, Nucleic Acids Res 18, 3871-3879), ASG-8 (MLL5; Emerling et al., 2002, Oncogene 21, 4849-54), ASG-9 (human mitochondrion encoding RNA), ASG-10 (signal recognition particle 9 kD; SRP9KD; (Lütcke, 1995, *Eur. J. Biochem.* 228, 531-550), and the novel ASG ASG-1.

4. DESCRIPTION OF THE FIGURES

FIG. 1. Schematic representation of the RaSH approach to the identification of AEGs as applied to HIV-1 infected early passage human fetal astrocytes. For this scheme tester (HIV-1 infected, 6 h, 12 h, and 24 h, and 3 d and 7 d) and driver (control uninfected, 6 h, 12 h, 24 h, and 3 d and 7 d) early passage human fetal astrocytes libraries were constructed followed by digestion of only the tester library with XhoI. After hybridization, differentially expressed sequences are cloned into XhoI-digested vectors, resulting in a subtracted cDNA library enriched for AEGs displaying reduced expression in human fetal astrocytes as a function of HIV-1 infection.

Figure 2:
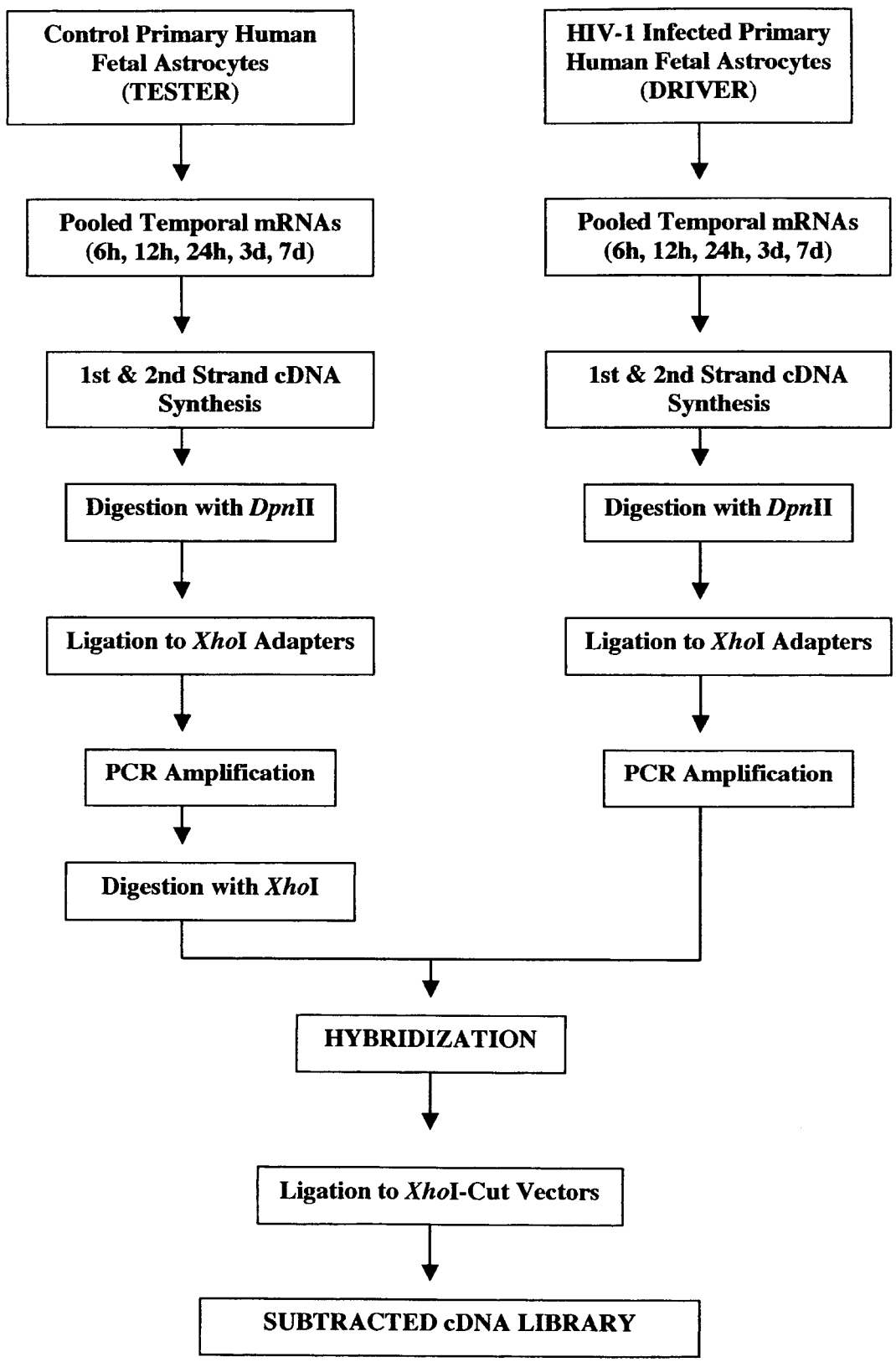

FIG. 2. Schematic representation of the RaSH approach to the identification of ASGs as applied to HIV-1 infected early passage human fetal astrocytes. For this scheme tester (control (mock-infected), 6 h, 12 h, and 24 h, and 3 d and 7 d) and driver (HIV-1-infected, 6 h, 12 h, 24 h, and 3 d and 7 d) early passage human fetal astrocytes libraries were constructed followed by digestion of only the tester library with XhoI. After hybridization, differentially expressed sequences are cloned into XhoI-digested vectors, resulting in a subtracted cDNA library enriched for ASGs displaying elevated expression in human fetal astrocytes as a function of HIV-1 infection.

Figure 3:
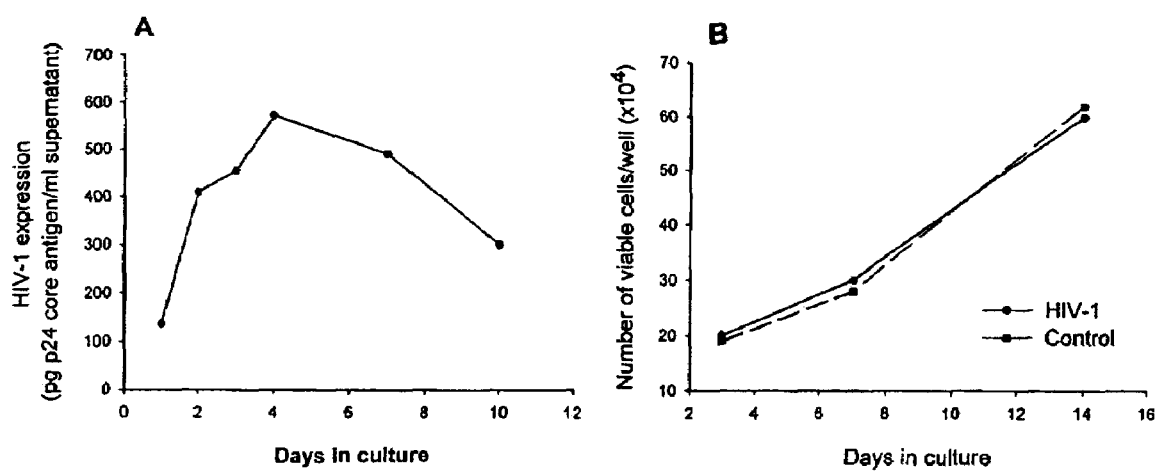

FIG. 3A-B. Infection of human fetal astrocytes with HIV-1 Astrocytes were infected with HIV-1 and tested for virus expression as described in Materials and Methods. (A) HIV-1 expression at various time points after infection. (B) Number of viable cells at various time points after infection.

Figure 4:
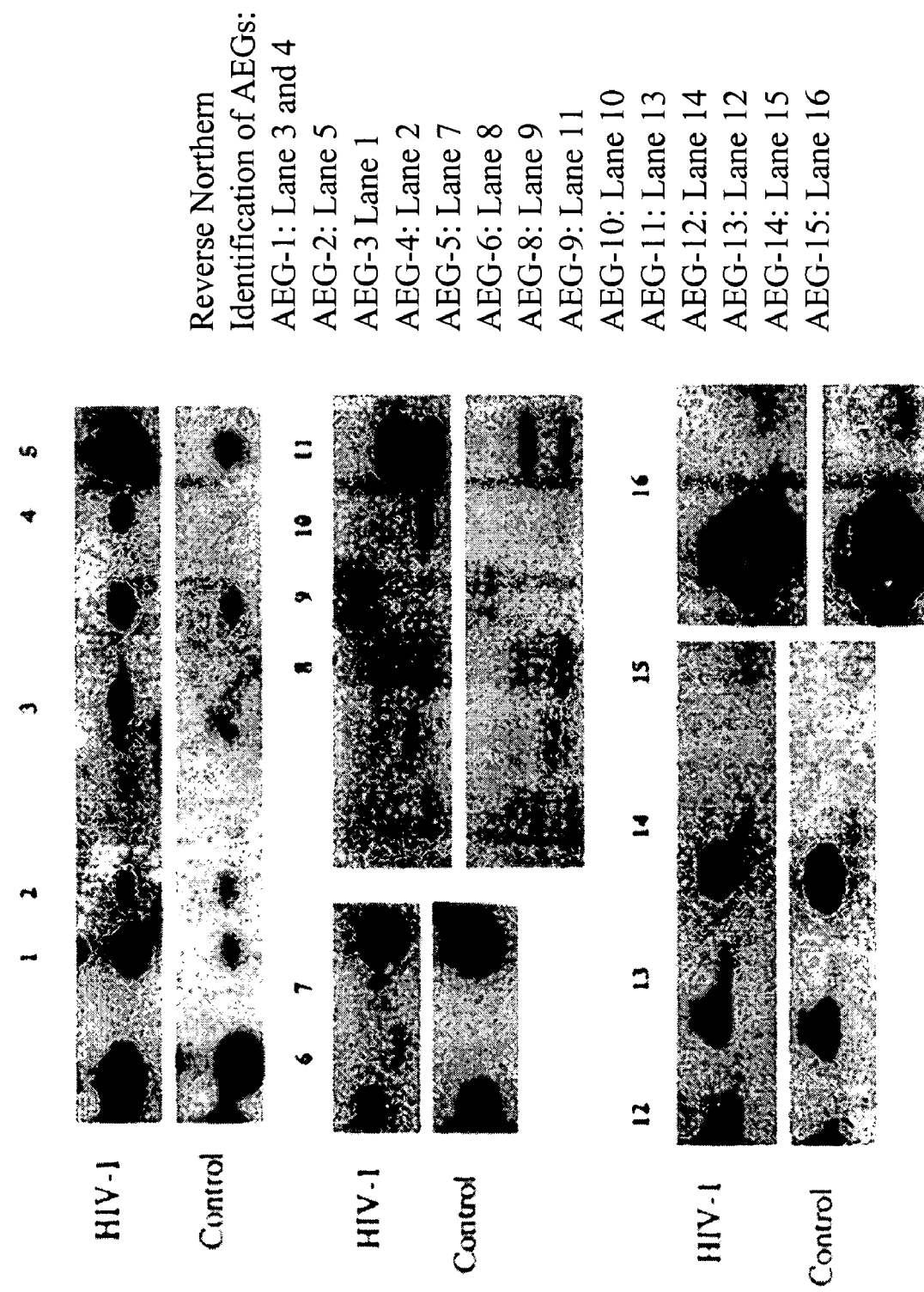

FIG. 4. Reverse Northern blot analysis of expressed sequence tags upregulated by HIV-1 infection as identified by RaSH. Equal quantities of PCR amplified products from random bacterial clones of RaSH-derived libraries were loaded onto 1.2% agarose gels. Samples were electrophoresed for 1 h under 100 V and transferred to nylon membranes. The blots were hybridized with $^{32}$P-labeled putative AEGs cDNAs reverse transcribed RNA samples. Blots were exposed for autoradiography. The lane numbers (1 to 10) indicate the various upregulated ESTs, which were designated AEG-1 to 15.

Figure 5:
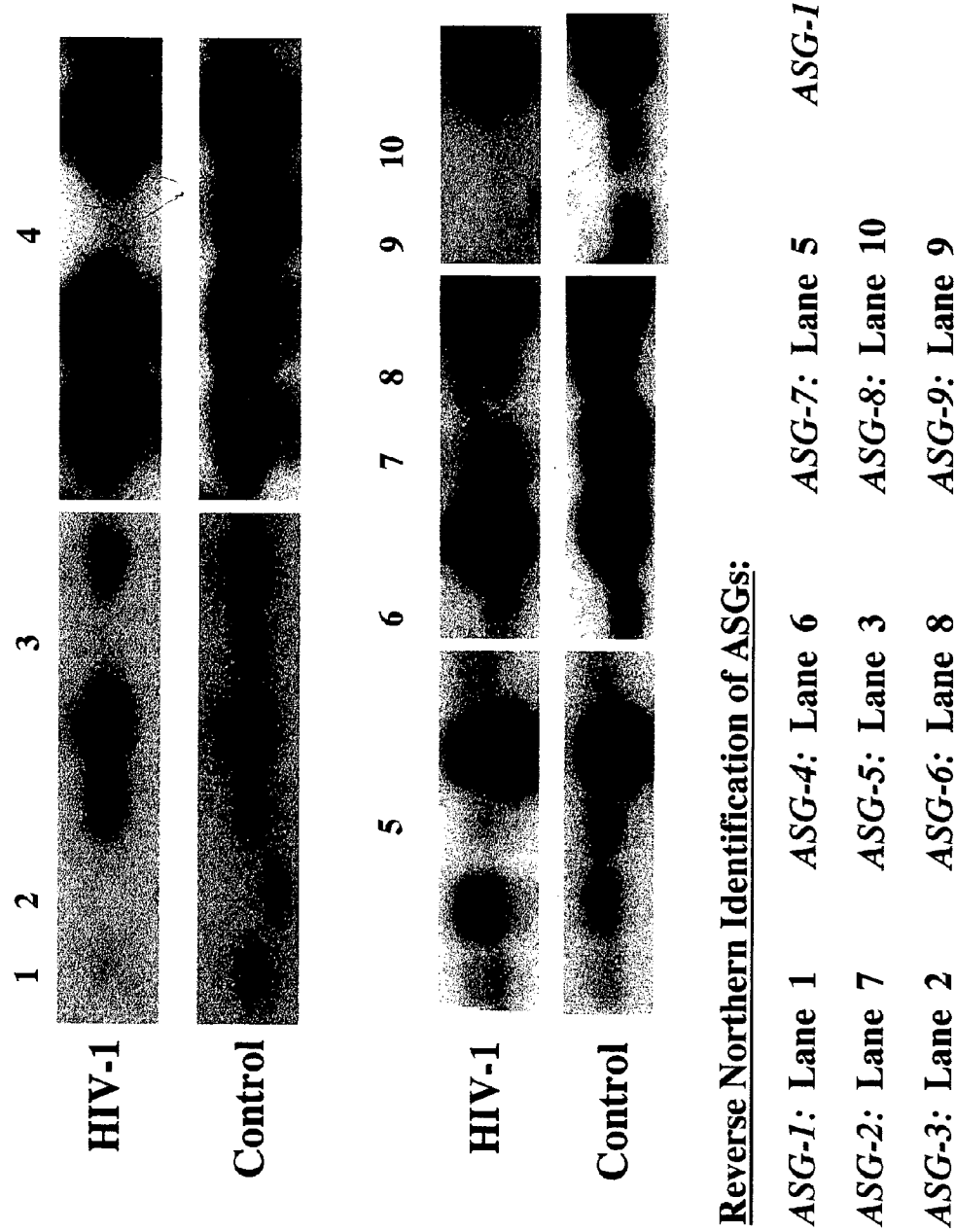

FIG. 5. Reverse Northern blot analysis of expressed sequence tags downregulated by HIV-1 infection as identified by RaSH. Equal quantities of PCR amplified products from random bacterial clones of RaSH-derived libraries were loaded onto 1.2% agarose gels. Samples were electrophoresed for 1 h under 100 V and transferred to nylon membranes. The blots were hybridized with $^{32}$P-labeled putative ASGs cDNAs reverse transcribed RNA samples. Blots were exposed for autoradiography. The lane numbers (1 to 10) indicate the various downregulated ESTs, which were designated ASG-1 to 10.

Figure 6:
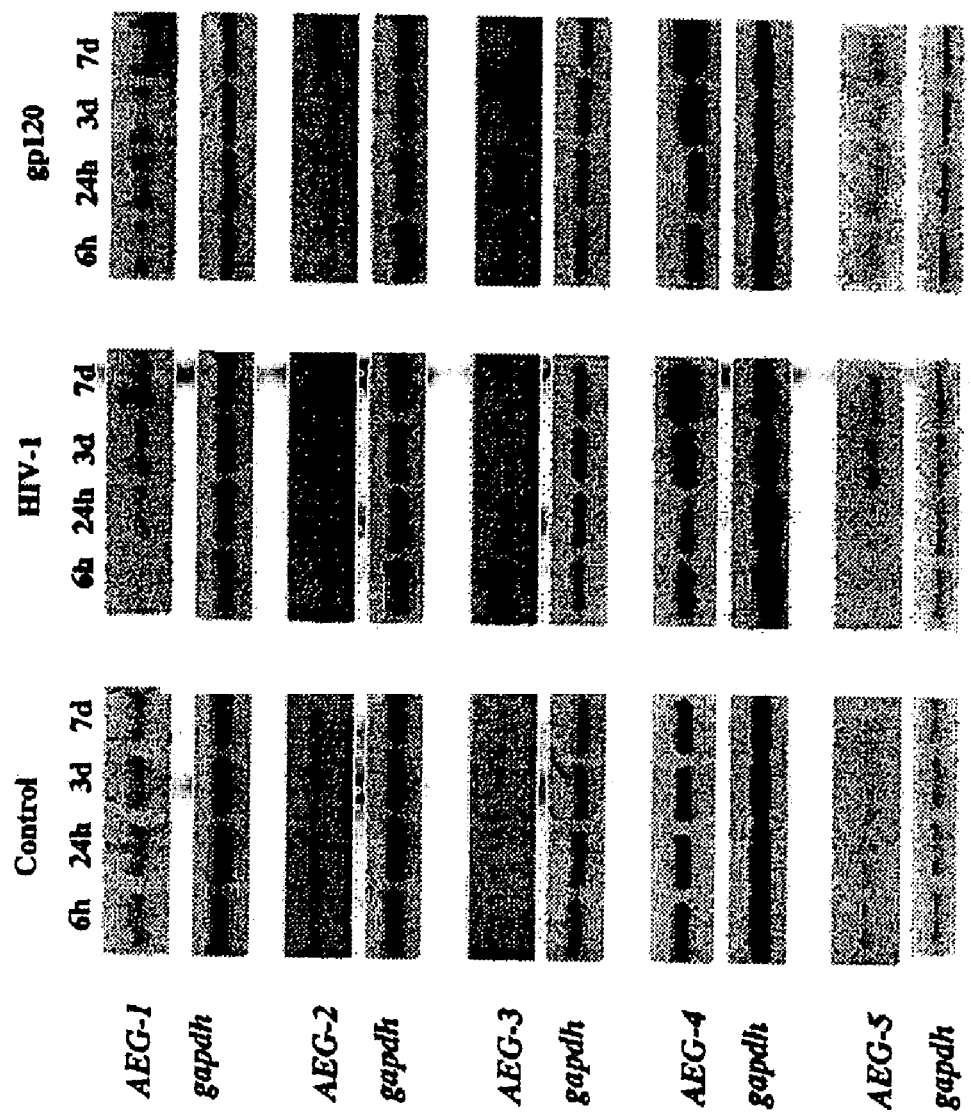

FIG. 6. Confirmation of differential expression using Northern blotting analysis of AEG-1 to AEG-5 displaying temporal elevated expression following HIV-1 infection or treatment with gp120. Early passage human fetal astrocytes were untreated (control), infected with HIV-1 at a multiplicity of infection (MOI) of 1, or treated with 1 nM gp120 for 6 h, 24 h, 3 d or 7 d, total RNA was isolated and analyzed by Northern blotting. Membranes were probed with the indicated radiolabeled [$^{32}$P] AEG EST, identified by RaSH, the blots were stripped and probed with a radiolabeled [$^{32}$P] gapdh cDNA probe. Expression was quantitated by densitometric analysis.

Figure 7:
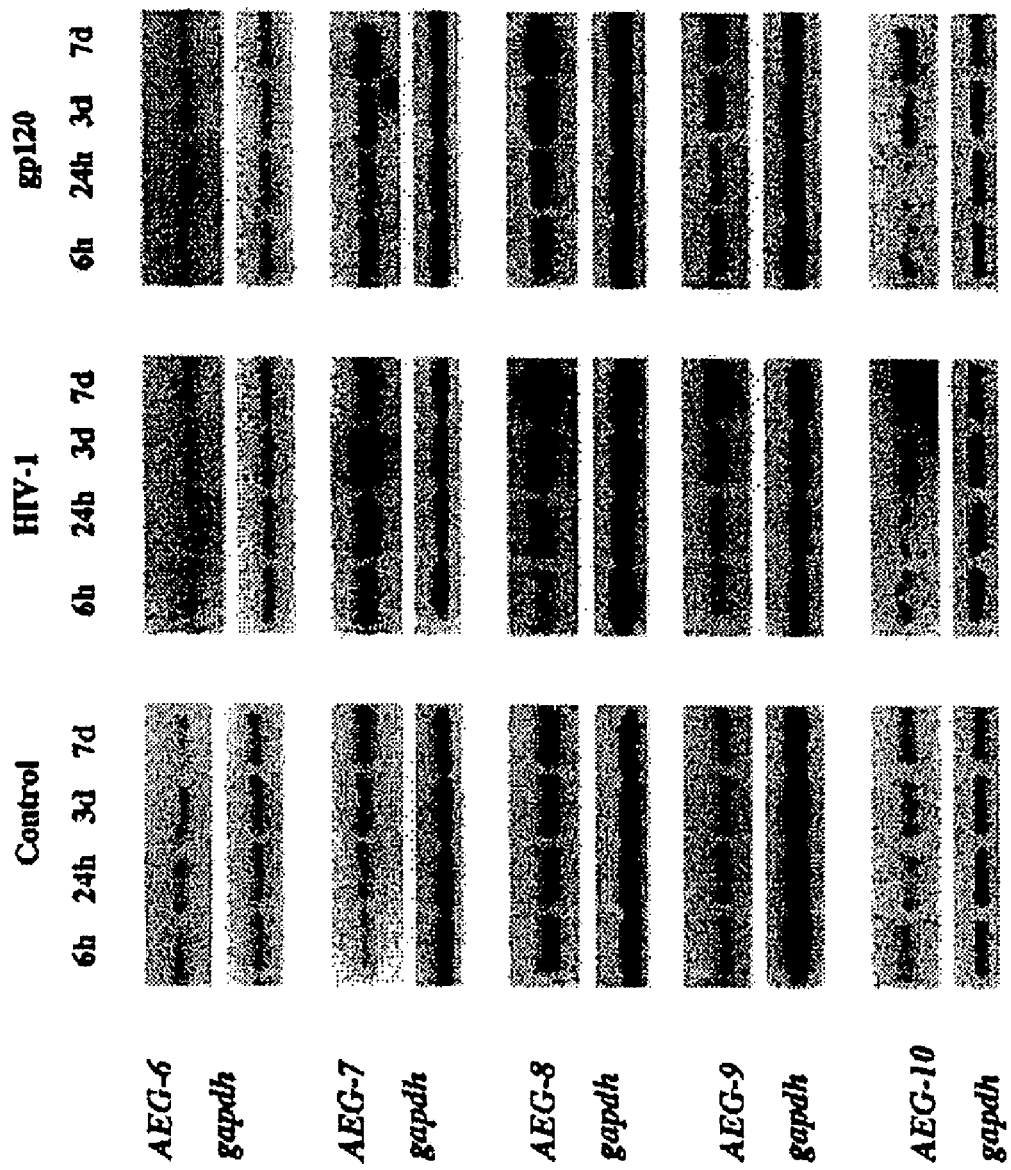

FIG. 7. Confirmation of differential expression using Northern blotting analysis of AEG-6 to AEG-10 displaying temporal elevated expression following HIV-1 infection or treatment with gp120. See "Materials and Methods" and FIG. 6 for experimental details.

Figure 8:
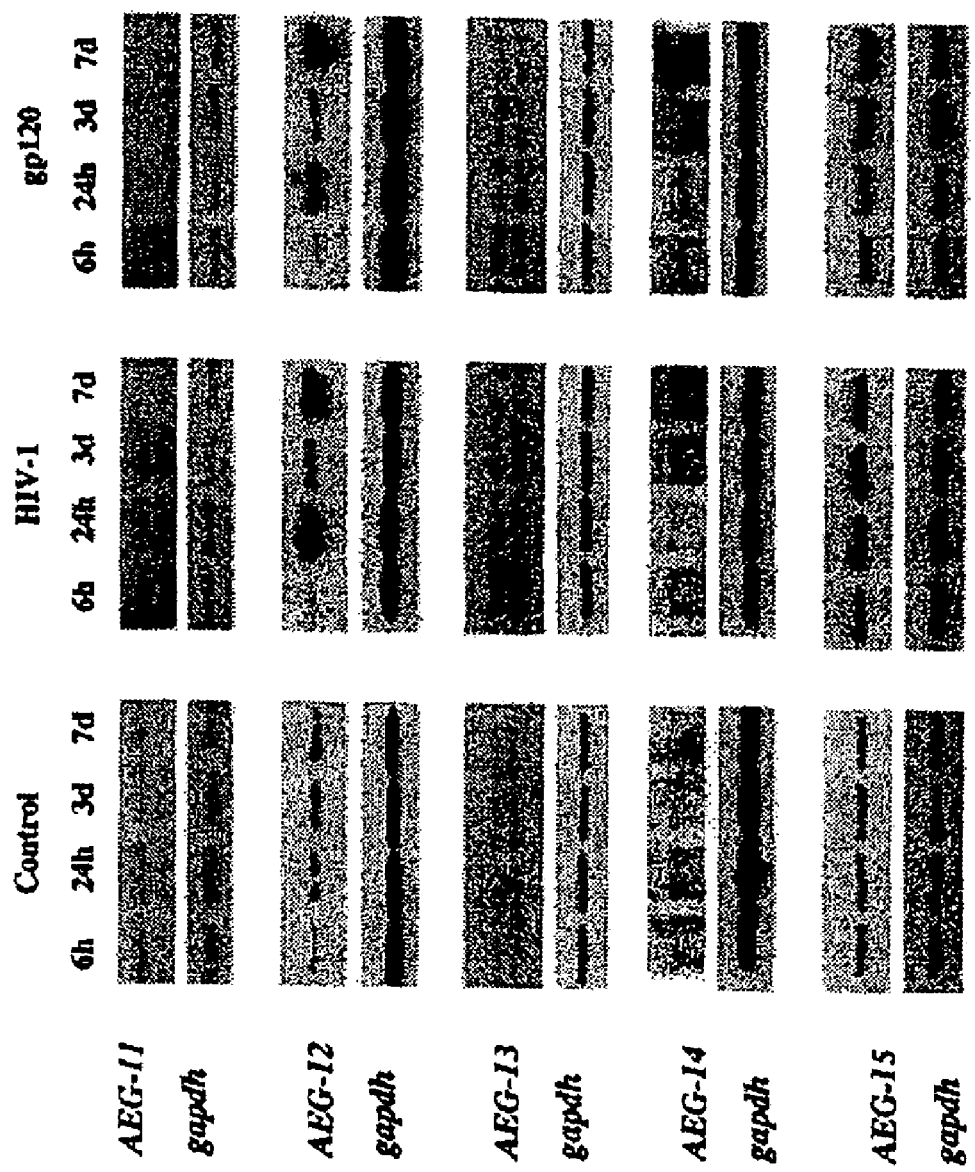

FIG. 8. Confirmation of differential expression using Northern blotting analysis of AEG-11 to AEG-15 displaying temporal elevated expression following HIV-1 infection or treatment with gp 120. See "Materials and Methods" and FIG. 6 for experimental details.

Figure 9:
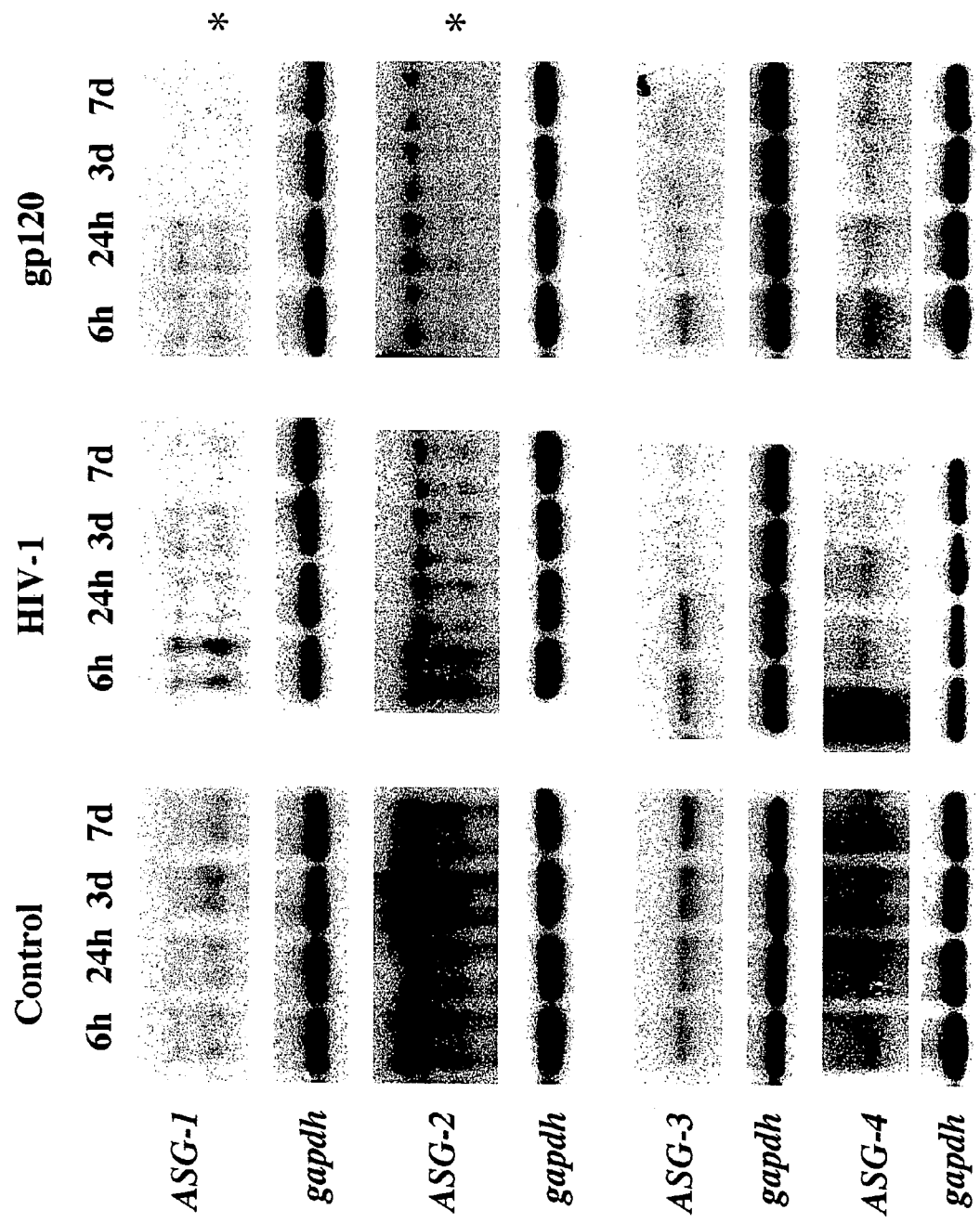

FIG. 9. Confirmation of differential expression using Northern blotting analysis of ASG-1 to ASG-4 displaying temporal elevated expression following HIV-1 infection or treatment with gp120. Early passage human fetal astrocytes were untreated (control), infected with HIV-1 at a multiplicity of infection (MOI) of 1, or treated with 1 nM gp120 for 6 h, 24 h, 3 d or 7 d, total RNA was isolated and analyzed by Northern blotting. Membranes were probed with the indicated radiolabeled [$^{32}$P] ASG EST, identified by RaSH, the blots were stripped and probed with a radiolabeled [$^{32}$P] gapdh cDNA probe. Expression was quantitated by densitometric analysis.

Figure 10:
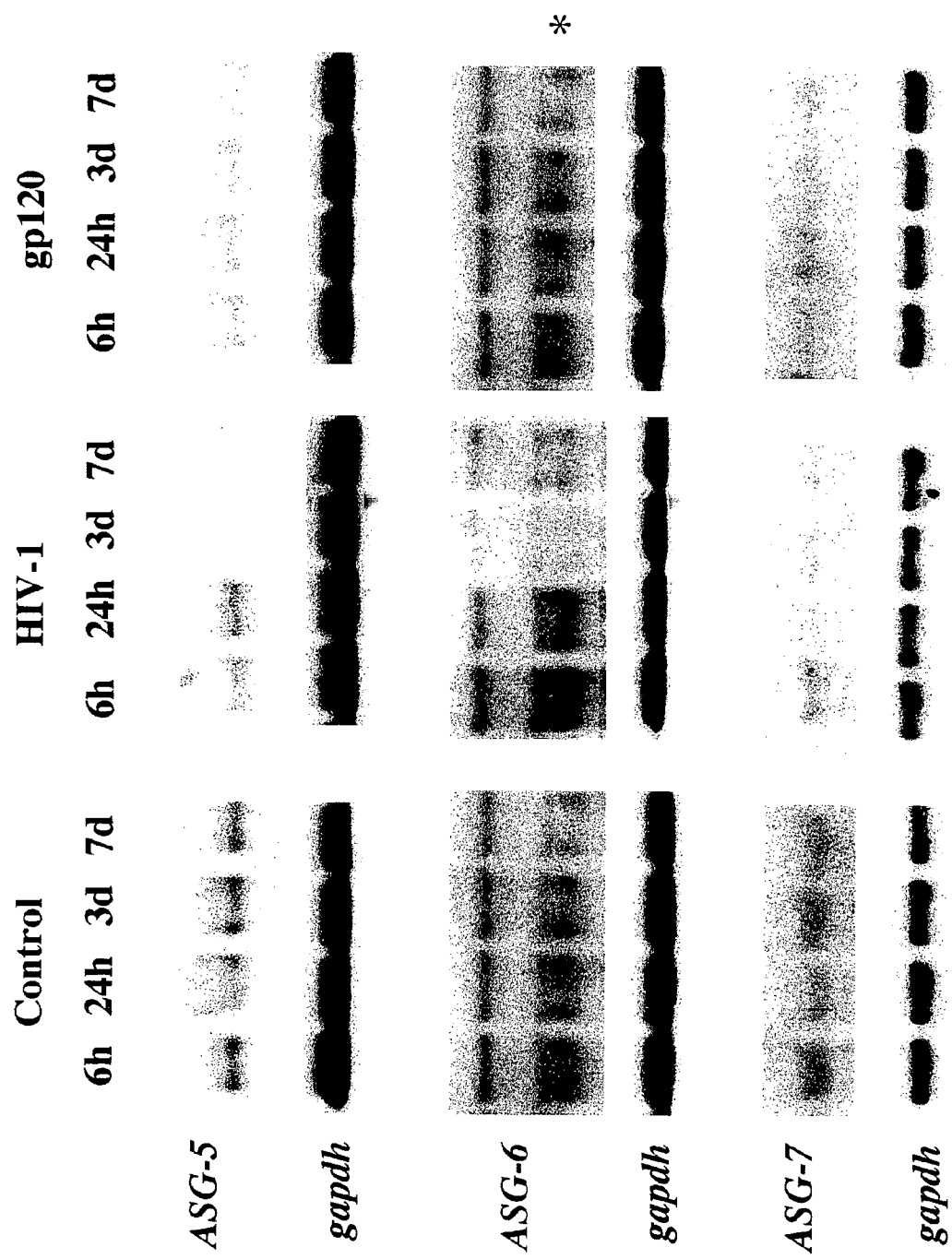

FIG. 10. Confirmation of differential expression using Northern blotting analysis of ASG-5 to ASG-7 displaying temporal elevated expression following HIV-1 infection or treatment with gp120. See "Materials and Methods" and FIG. 6 for experimental details.

Figure 11:
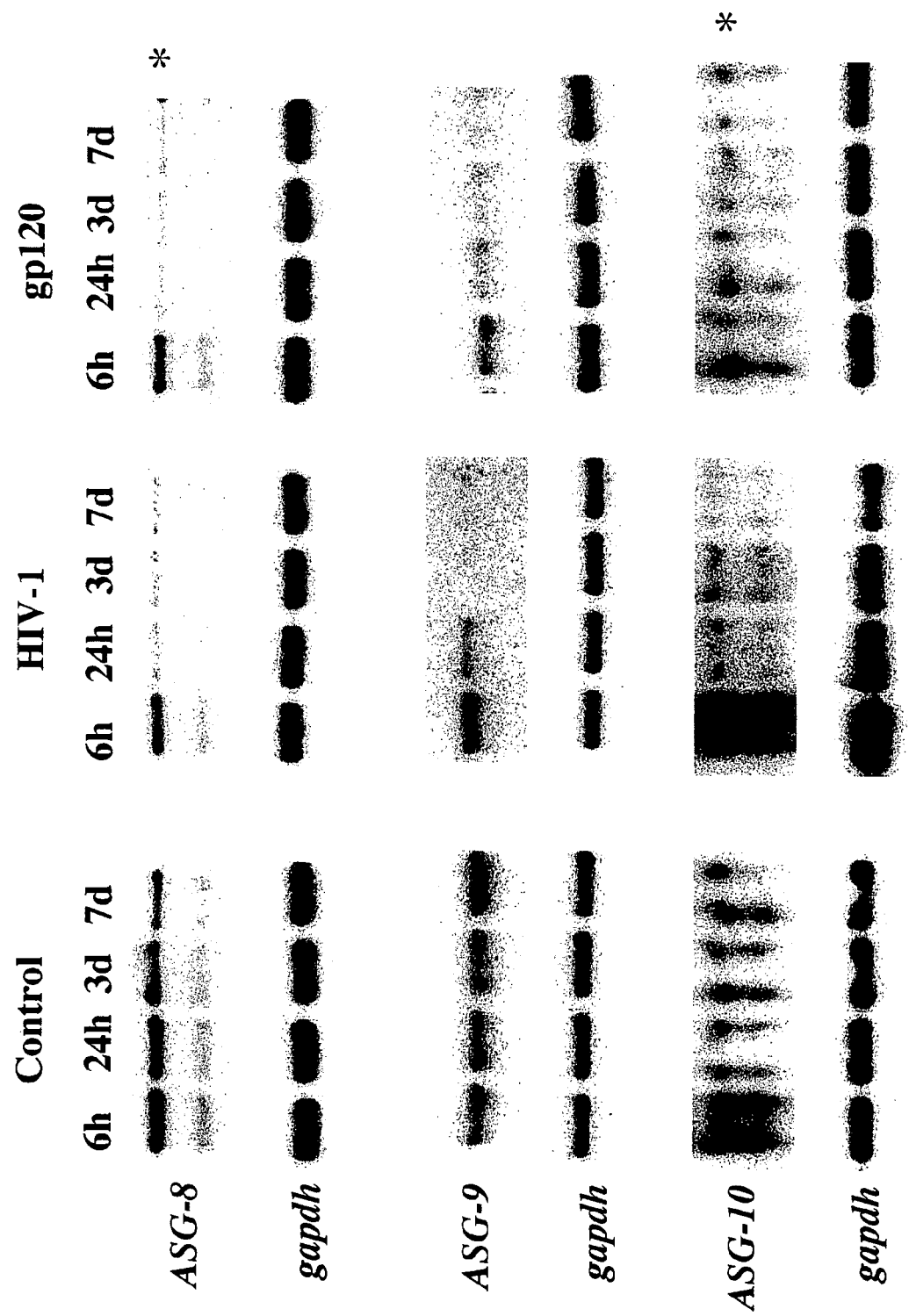

FIG. 11. Confirmation of differential expression using Northern blotting analysis of ASG-8 to ASG-10 displaying temporal elevated expression following HIV-1 infection or treatment with gp120. See "Materials and Methods" and FIG. 6 for experimental details.

Figure 12:
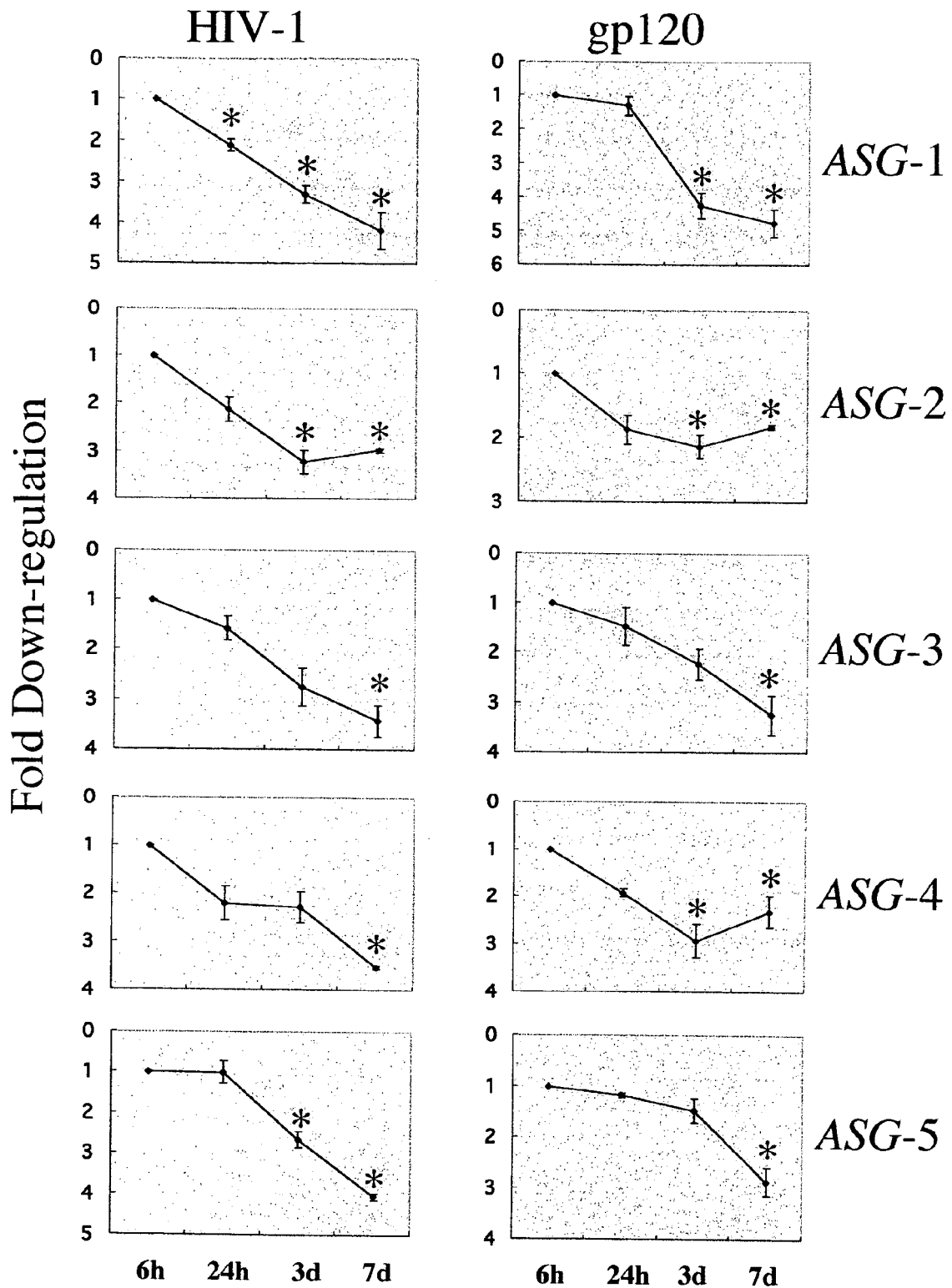
Figure 12:
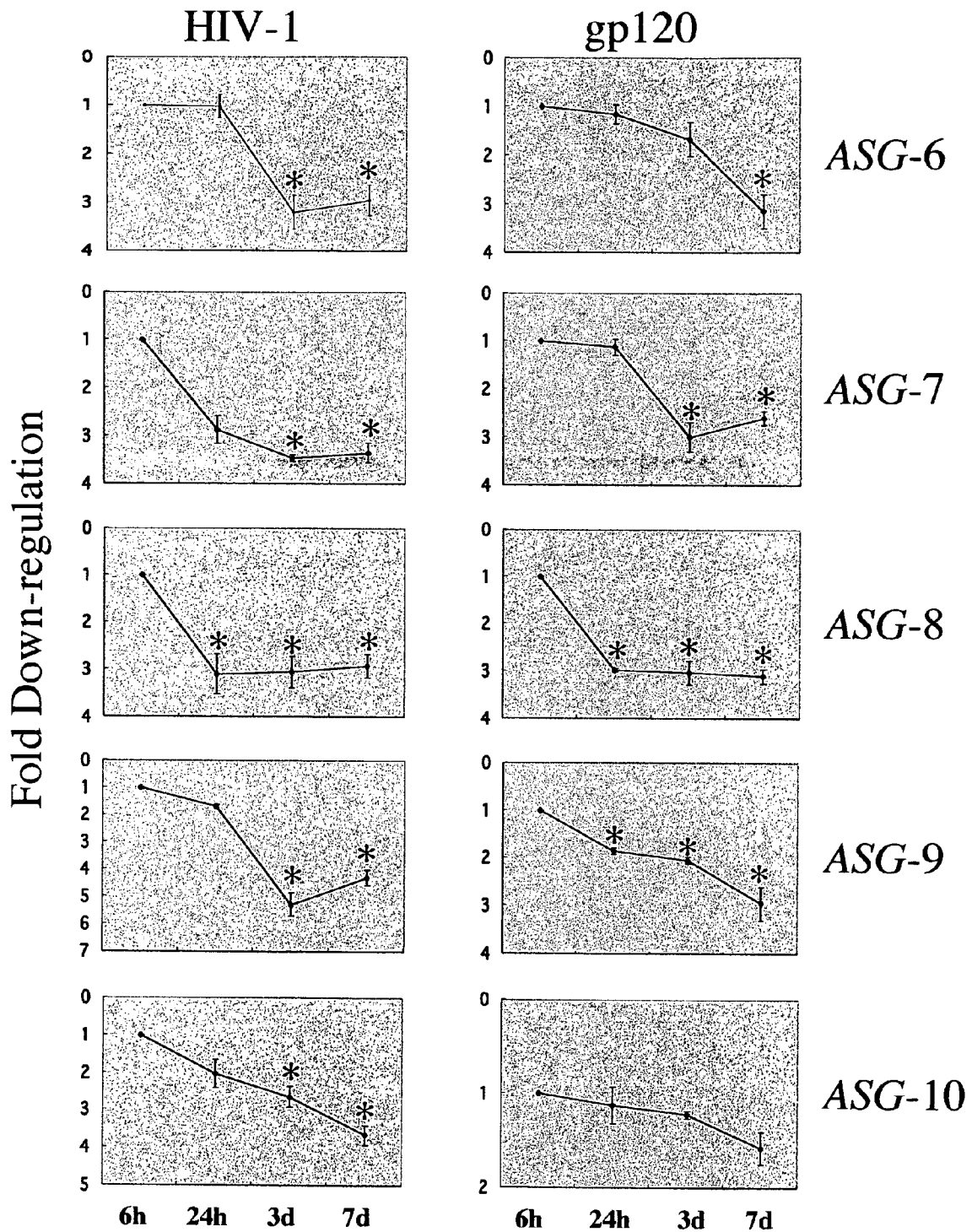

FIG. 12. Temporal modulation of ASG expression in normal human fetal astrocytes as a consequence of infection with HIV-1 or exposure to gp120. Data presented reflects values obtained after scanning and normalizing (to gapdh) the Northern blots shown in FIGS. 9-11. Fold-decline in expression was determined as described in the legend to Table 1.

FIG. 13A-B. Expression of AEG-6 and AEG-13 proteins in HIV-1 infected and control astrocytes as determined by Western blotting. Astrocytes were infected with HIV-1 at a MOI of 1 or equal to 1 nM gp120, and treated and untreated cells were cultured and sampled at the designated times for immunoblot analysis as described in "Materials and Methods". Asterisks indicate a double amount of cell lysate loaded per lane. Panel A and Panel B represent studies using two independently derived early passage human fetal astrocyte cultures.

FIG. 14. Nucleic acid sequence of the AEG-1 cDNA (SEQ ID NO:1).

FIG. 15. Amino acid sequence of the AEG-1 protein (SEQ ID NO:2).

FIG. 16. Nucleic acid sequence of the AEG-11 DNA (SEQ ID NO:3).

FIG. 17. Nucleic acid sequence of the ASG-1 DNA (SEQ ID NO:4).

5. DETAILED DESCRIPTION OF THE INVENTION

The present invention relates to compositions and/or methods which contain and/or utilize AMG nucleic acid molecules, proteins, or related reagents. The nucleic acid molecules of the invention may or may not comprise protein-encoding sequences. For clarity of presentation, and not by way of limitation, the detailed description is divided into the following subsections:

(i) AMG nucleic acids;
(ii) AMG proteins;
(iii) anti-AMG antibodies;
(iv) screening methods; and
(v) methods of diagnosis and treatment.

5.1. AMG Nucleic Acids

The present invention provides for nucleic acid molecules corresponding to AMGs, which may comprise AEGs or ASGs. The nucleic acid molecules of the invention include but are not limited to "full-length" nucleic acid molecules which contain, in DNA or RNA form, a complete protein coding sequence, in sense or antisense orientation. The nucleic acid molecules of the invention also include molecules which are not "full-length" but which represent, in DNA or RNA form, a portion of an mRNA molecule, which may constitute protein coding and/or untranslated regions in sense or antisense orientation; such molecules may be useful as probes for detecting RNA levels, as PCR primers or as antisense inhibitors.

In particular non-limiting embodiments, the present invention provides for nucleic acid molecules of the following AEGs: AEG-2 (G-binding protein), AEG-3 (GA17 protein) (Ryo et al., 2000, *AIDS Res. Hum. Retroviruses* 16, 995-1005), AEG-4 (unr/NRU) (Jeffers et al., 1990, *Nucl. Acids. Res.* 18, 4891-4899; Boussadia et al., 1993, *Biochim. Biophys. Acta* 1172, 64-72), AEG-5 (hGNT-IV-H) (Furukawa et al., 1999, *J. Hum. Genet.* 44, 397-401), AEG-6 (fibronectin), AEG-7 (human CTL2) (O'Regan et al., 2000, *Proc. Natl. Acad. Sci. USA* 97, 1835-1840), AEG-8 (acidic ribosomal phosphoprotein) (Rich & Stietz, 1987, *Mol. Cell. Biol.* 7, 4065-4074), AEG-9 (calnexin) (Honore et al., 1994, *Electrophoresis* 15, 482-490; Rubio & Wenthold, 1999, *J. Neurochem.* 73, 942-948; Shi et al., 2001, *Cell* 105, 331-342), AEG-10 (autotaxin) (Stracke et al., 1994, *J. Biol. Chem.* 267, 2524-2529; Kawagoe et al., 1997, *Cancer Res.* 57, 2516-25), AEG-12 (thymosin β-4) (Gondo et al., 1987, *J. Immunol.* 139, 3840-3848), AEG-13 (human non-muscle α-actinin) (Yousoufian et al., 1990, *Am. J. Hum. Genet.* 47, 62-72), AEG-14 (Schneider et al., 1988, *Cell* 54, 787-793; Gonos, 1998, *Ann. N.Y. Acad. Sci.* 851, 466-469; Prieto et al., 1999, *Brain Res.* 816, 646-661) and AEG-15 (PGK-1) (Michelson et al., 1983, *Proc. Natl. Acad. Sci. USA* 80, 472-476; Tsukada et al., 1991, *J. Gerontol.* 46, B213-B216), and the novel AEGs AEG-1 and AEG-11. The present invention further provides for nucleic acid molecules which hybridize to these nucleic acid molecules under stringent conditions, having lengths of at least 15 nucleotides and preferably at least 50 nucleotides.

In other non-limiting embodiments, the present invention provides for nucleic acid molecules encoding the novel AEGs AEG-1 and AEG-11. For example, the present invention provides for nucleic acid molecules having the sequence set forth as SEQ ID NO:1 or as SEQ ID NO:3, as depicted in FIG. 14 and FIG. 16, respectively, or their complementary strands. The present invention further provides for nucleic acid molecules that are between 15 and 500 nucleotides in length, preferably between 50 and 1000 nucleotides in length, and more preferably between 1000 and 10,000 nucleotides in length, which hybridize to a molecule having SEQ ID NO:1 or SEQ ID NO:3 or their complementary strands under stringent conditions. The present invention further provides for nucleic acid molecules which encode a protein having an amino acid sequence as set forth as SEQ ID NO:2 and depicted in FIG. 15, their complementary strands, and nucleic acid molecules which hybridize under stringent conditions to their sense or antisense strands. No specific protein product has yet been identified for the AEG-11 gene, consistent with a cellular function for the RNA product of this gene.

In particular non-limiting embodiments, the present invention also provides for nucleic acid molecules of the following ASGs: ASG-2 (human cDNA FLJ10705; GenBank Acc. No. AK001567, ASG-3 (Platelet-endothelial cell tetra-span antigen 3; CD151/PETA-3; Fitter et al., 1995, *Blood* 86, 1348-55; Yáñez-Mó et al., 1998, *J. Cell Biol.* 141, 791-804), ASG-4 (guanine nucleotide-releasing factor; C3G; Schweighoffer et al., 1993, *Oncogene* 8, 1477-85; Tanaka et al., 1994, *Proc. Natl. Acad. Sci. USA* 91, 3443-3447), ASG-5 (neuronatin; ASG-5, Dou & Joseph, 1996, *Brain Res.* 723, 8-22; Usui et al., 1997, *J. Mol. Neurosci.* 9, 55-60), ASG-6 (neuroendocrine differentiation factor; CGI149; Wilson et al., 2001, *J. Clin. Endocrinol. Metab.* 86, 4504-11), ASG-7 (cysteine/glycine-rich protein 1; CSRP1; Liebhaber et al. 1990, Nucleic Acids Res 18, 3871-3879), ASG-8 (MLL5; Emerling et al., 2002, Oncogene 21, 4849-54), ASG-9 (human mitochondrion encoding RNA), ASG-10 (signal recognition particle 9 kD; SRP9KD; (Lütcke, 1995, Eur. J. Biochem. 228, 531-550), and the novel ASG ASG-1. The present invention further provides for nucleic acid molecules which hybridize to these nucleic acid molecules under stringent conditions, having lengths of at least 15 nucleotides and preferably at least 50 nucleotides.

In other non-limiting embodiments, the present invention provides for nucleic acid molecules for the novel ASG ASG-1. For example, the present invention provides for nucleic acid molecules having the sequences set forth as SEQ ID NO:4, as depicted in FIG. 17, or its complementary strand. The present invention further provides for nucleic acid molecules that are between 15 and 500 nucleotides in length, preferably between 50 and 1000 nucleotides in length, and more preferably between 1000 and 10,000 nucleotides in length, which hybridize to molecules having SEQ ID NO:4 or its complementary strand under stringent conditions. The present invention further provides for nucleic acid molecules which encode the protein products of the nucleic acid sequence set forth as SEQ ID NO:4, its complementary strand, and nucleic acid molecules which hybridize under stringent conditions to its sense or antisense strands.

Any aforesaid nucleic acid molecule may be linked to a heterologous nucleic acid, as discussed, for example, below.

For some purposes, an AMG may be engineered such that it is in an "expressible form." An "expressible form" is one in which an AMG is linked to one or more elements necessary or desirable for transcription and/or translation. For example, the AMG nucleic acid may be operatively linked to a suitable promoter element in an expression cassette which may further comprise a transcription initiation and termination site, nucleic acid encoding a nuclear localization sequence, a ribosome binding site, a polyadenylation site, and/or a mRNA stabilizing sequence, etc.

Examples of suitable promoter elements, include, but are not limited to, the cytomegalovirus immediate early promoter, the Rous sarcoma virus long terminal repeat promoter, the human elongation factor-1α promoter, the human ubiquitin c promoter, etc. It may be desirable, in certain embodiments of the invention, to use a regulatable promoter. Non-limiting examples of regulatable promoters include the murine mammary tumor virus promoter (inducible with dexamethasone), commercially-available steroid- or tetracycline-responsive promoters, or ecdysone-inducible promoters, etc. It may further be desirable, in certain embodiments of the invention, to use astrocyte-specific promoters. Non-limiting examples of astrocyte-specific promoters include the specific glial fibrillary acidic protein (GFAP) promoter, the murine cytomegalovirus immediate-early (MCMV-IE) gene promoter, and the alpha tubulin promoter. Other suitable constitutive, regulatable, or cell- or tissue-specific promoter systems are known to those of ordinary skill in the art.

A nucleic acid molecule of the invention, whether or not it is to be expressed as a protein, may be inserted into a suitable vector for duplication purposes. Suitable vectors include but are not limited to plasmids, cosmids, phages, phagemids, artificial chromosomes, replicons, and various virus-based vector systems known in the art.

Where an AMG protein or peptide is to be expressed, suitable expression vectors include virus-based vectors and non-virus based DNA or RNA delivery systems. Examples of appropriate virus-based gene transfer vectors include, but are not limited to, those derived from retroviruses, for example Moloney murine leukemia-virus based vectors such as LX, LNSX, LNCX or LXSN (Miller and Rosman, 1989, *Biotechniques* 7, 980-989); lentiviruses, for example human immunodeficiency virus ("HIV"), feline leukemia virus ("FIV") or equine infectious anemia virus ("EIAV")-based vectors (Case et al., 1999, *Proc. Natl. Acad. Sci. USA* 96, 2988-2993; Curran et al., 2000, *Molecular Ther.* 1, 31-38; Olsen, 1998, *Gene Ther.* 5, 1481-1487); adenoviruses (Zhang, 1999, *Cancer Gene Ther.* 6, 113-138; Connelly, 1999, *Curr. Opin. Mol. Ther.* 1, 565-572), for example Ad5/CMV-based E1-deleted vectors (Li et al., 1993, *Human Gene Ther.* 4, 403-409); adeno-associated viruses, for example pSub201-based AAV2-derived vectors (Walsh et al., 1992, *Proc. Natl. Acad. Sci. U.S.A.* 89, 7257-7261); herpes simplex viruses, for example vectors based on HSV-1 (Geller & Freese, 1990, *Proc. Natl. Acad. Sci. U.S.A.* 87, 1149-1153); baculoviruses, for example AcMNPV-based vectors (Boyce & Bucher, 1996, *Proc. Natl. Acad. Sci. U.S.A.* 93, 2348-2352); SV40, for example SVluc (Strayer & Milano, 1996, *Gene Ther.* 3, 581-587); Epstein-Barr viruses, for example EBV-based replicon vectors (Hambor et al., 1988, *Proc. Natl. Acad. Sci. U.S.A.* 85, 4010-4014); alphaviruses, for example Semliki Forest virus- or Sindbis virus-based vectors (Polo et al., 1999, *Proc. Natl. Acad. Sci. U.S.A.* 96, 4598-4603); vaccinia viruses, for example modified vaccinia virus (MVA)-based vectors (Sutter & Moss, 1992, *Proc. Natl. Acad. Sci. U.S.A.* 89, 10847-10851) or any other class of viruses that can efficiently transduce human tumor cells and that can accommodate the nucleic acid sequences required for therapeutic efficacy.

Non-limiting examples of non-virus-based delivery systems that may be used according to the invention include, but are not limited to, so-called naked nucleic acids (Wolff et al., 1990, *Science* 247, 1465-1468), nucleic acids encapsulated in liposomes (Nicolau et al., 1987, *Methods in Enzymology* 149, 157-176), nucleic acid/lipid complexes (Legendre & Szoka, 1992, *Pharmaceutical Research* 9, 1235-1242), and nucleic acid/protein complexes (Wu & Wu, 1991, *Biother.* 3, 87-95).

AMGs may also be produced using nucleic acid contained in plasmids, such as pCEP4 (Invitrogen, San Diego, Calif.), pMAMneo (Clontech, Palo Alto, Calif.; see below), pcDNA3.1 (Invitrogen, San Diego, Calif.), etc. Vectors useful in expressing AMG-1 in bacterial systems include but are not limited to the GST vector (Amersham) and the chitin binding domain vector (TYB-12) (New England Biolabs).

In a preferred embodiment, an AMG vector comprises the AEG-1 gene of SEQ ID NO:1 operatively linked to a heterologous regulatory element and a polyadenylation signal, both of which are active in mammalian cells. The resulting expression cassette may be contained within a plasmid or a virus-based vector. In preferred embodiments, the expression cassette is contained within an adenovirus vector derived from human adenovirus type 2 or 5, or within an adeno-associated virus (AAV) vector derived from human AAV2.

5.2. AMG Proteins

The present invention provides for AMG proteins. These include, but are not limited to, the following AEG proteins: AEG-2 (G-binding protein), AEG-3 (GA17 protein) (Ryo et al., 2000, *AIDS Res. Hum. Retroviruses* 16, 995-1005), AEG-4 (unr/NRU) (Jeffers et al., 1990, *Nucl. Acids. Res.* 18, 4891-4899; Boussadia et al., 1993, *Biochim. Biophys. Acta* 1172, 64-72), AEG-5 (hGNT-IV-H) (Furukawa et al., 1999, *J. Hum. Genet.* 44, 397-401), AEG-6 (fibronectin), AEG-7 (human CTL2) (O'Regan et al., 2000, *Proc. Natl. Acad. Sci. USA* 97, 1835-1840), AEG-8 (acidic ribosomal phosphoprotein) (Rich & Stietz, 1987, *Mol. Cell. Biol.* 7, 4065-4074), AEG-9

(calnexin) (Honore et al., 1994, *Electrophoresis* 15, 482-490; Rubio & Wenthold, 1999, *J. Neurochem.* 73, 942-948; Shi et al., 2001, *Cell* 105, 331-342), AEG-10 (autotaxin) (Stracke et al., 1994, *J. Biol. Chem.* 267, 2524-2529; Kawagoe et al., 1997, *Cancer Res.* 57, 2516-25), AEG-12 (thymosin β-4) (Gondo et al., 1987, *J. Immunol.* 139, 3840-3848), AEG-13 (human non-muscle α-actinin) (Youssoufian et al., 1990, *Am. J. Hum. Genet.* 47, 62-72), AEG-14 (Schneider et al., 1988, *Cell* 54, 787-793; Gonos, 1998, *Ann. N.Y. Acad. Sci.* 851, 466-469; Prieto et al., 1999, *Brain Res.* 816, 646-661) and AEG-15 (PGK-1) (Michelson et al., 1983, *Proc. Natl. Acad. Sci. USA* 80, 472-476; Tsukada et al., 1991, *J. Gerontol.* 46, B213-B216). The invention also encompasses peptide fragments of these AEG proteins comprising at least 20 amino acids which cross-react with an immunoglobulin which specifically binds to the corresponding full-length protein.

In specific, non-limiting embodiments, the present invention provides for proteins encoded by nucleic acids AEG-1 and AEG-11. In one particular embodiment, the invention provides for a protein encoded by a nucleic acid sequence as set forth in SEQ ID NO:1 (depicted in FIG. 14), and specifically for a protein having an amino acid sequence as set forth in SEQ ID NO:2 (FIG. 15). The invention further encompasses peptide fragments of such proteins comprising at least 20 amino acids which cross-react with an immunoglobulin which specifically binds to a full-length AEG-1 or AEG-11 protein.

The present invention also provides for ASG proteins, including, but not limited to, the following: ASG-2 (human cDNA FLJ10705; GenBank Acc. No. AK001567, ASG-3 (Platelet-endothelial cell tetra-span antigen 3; CD151/PETA-3; Fitter et al., 1995, *Blood* 86, 1348-55; Yáñez-Mó et al., 1998, *J. Cell Biol.* 141,791-804), ASG-4 (guanine nucleotide-releasing factor; C3G; Schweighoffer et al., 1993, *Oncogene* 8, 1477-85; Tanaka et al., 1994, *Proc. Natl. Acad. Sci. USA* 91, 3443-3447), ASG-5 (neuronatin; ASG-5; Dou & Joseph, 1996, *Brain Res.* 723, 8-22; Usui et al., 1997, *J. Mol. Neurosci.* 9, 55-60), ASG-6 (neuroendocrine differentiation factor; CGI149; Wilson et al., 2001, *J. Clin. Endocrinol. Metab.* 86, 4504-11), ASG-7 (cysteine/glycine-rich protein 1; CSRP 1; Liebhaber et al. 1990, *Nucleic Acids Res* 18, 3871-3879), ASG-8 (MLL5; Emerling et al., 2002, *Oncogene* 21, 4849-54), ASG-9 (human mitochondrion encoding RNA), ASG-10 (signal recognition particle 9 kD; SRP9KD; (Lütcke, 1995, *Eur. J. Biochem.* 228, 531-550), and the novel ASG ASG-1. The invention also encompasses peptide fragments of these ASG proteins comprising at least 20 amino acids which cross-react with an immunoglobulin which specifically binds to the corresponding full-length protein.

In specific, non-limiting embodiments, the present invention provides for proteins encoded by ASG-1 nucleic acids. In one particular embodiment, the invention provides for a protein encoded by nucleic acid sequences as set forth in SEQ ID NO:4 (depicted in FIG. 17). The invention further encompasses peptide fragments of such proteins comprising at least 20 amino acids which cross-react with an immunoglobulin which specifically binds to a full-length ASG-1 protein.

The AMG proteins and peptides of the invention may be prepared by standard techniques, including recombinant DNA-related techniques and chemical synthesis, or by collection from natural sources. For recombinant DNA expression, a non-limiting list of suitable expression vectors is set forth in the preceding section.

Expression systems which may be used to produce AMG proteins include prokaryotic and eukaryotic expression systems, including eukaryotic cells, bacteria, fungi (e.g. yeast), insects, etc. Depending on the expression system used, nucleic acid may be introduced by any standard technique, including transfection, transduction, electroporation, bioballistics, microinjection, etc.

5.3. Anti-AMG Antibodies

The present invention also provides for antibody molecules which react with AMG proteins and peptides. In specific, non-limiting examples, the invention provides for antibody molecules (as defined infra) which bind specifically to proteins having an amino acid sequence as set forth in SEQ ID NO:2 (AEG-1). According to the invention, an AMG protein or peptide, derivatives (e.g. a histidine-tagged protein), or analogs thereof, may be used as an immunogen to generate antibodies. Such antibodies include, but are not limited to, polyclonal, monoclonal, chimeric, single chain, Fab fragments, and a Fab expression library.

Various procedures known in the art may be used for the production of polyclonal antibodies which specifically bind to an AMG protein or peptide. For the production of antibodies, various host animals can be immunized by injection with the protein or peptide, including but not limited to rabbits, mice, rats, goats, etc. Various adjuvants may be used to increase the immunological response, depending on the host species, and including but not limited to Freund's (complete or incomplete) adjuvant, mineral gels such as aluminum hydroxide, surface active substances such as lysolecithin, pluronic polyols, polyanions, peptides, oil emulsions, keyhole limpet hemocyanins, dinitrophenol, and potentially useful human adjuvants such as BCG (Bacille Calmette-Guerin) and *Corynebacterium parvum*.

For preparation of monoclonal antibodies directed toward an AMG protein or polypeptide fragments thereof, any technique which provides for the production of antibody molecules by continuous cell lines in culture also may be used. Examples of such techniques include the hybridoma technique originally developed by Kohler & Milstein (1975, *Nature* 256, 495-497), as well as the trioma technique, the human B-cell hybridoma technique (Kozbor et al., *Immunology Today* 1983;4, 72-79), and the EBV hybridoma technique to produce human monoclonal antibodies (Cole et al., in Monoclonal Antibodies and Cancer Therapy, Alan R. Liss, Inc., 1985, pp. 77-96). In an additional embodiment of the invention, monoclonal antibodies can be produced in germ-free animals utilizing the technology disclosed in International Patent Application PCT/US89/02545. According to the invention, human antibodies may be used and can be obtained by using human hybridomas (Cote et al., 1983, *Proc. Natl. Acad. Sci. U.S.A.* 80, 2026-2030) or by transforming human B cells with EBV virus in vitro (Cole et al., in Monoclonal Antibodies and Cancer Therapy, Alan R. Liss, 1985, pp. 77-96). Further, according to the invention, techniques developed for the production of "chimeric antibodies" (Morrison et al., 1984, *Proc. Nat. Acad. Sci. U.S.A.* 81, 6851-6855; Neuberger et al., 1984, *Nature* 312, 604-608; Takeda et al., 1985, *Nature* 314, 452-454) by splicing the genes from a mouse antibody molecule specific for an AMG protein or peptide together with genes from a human antibody molecule of appropriate biological activity may be used; such antibodies are within the scope of this invention.

According to the invention, techniques described for the production of single chain antibodies (U.S. Pat. No. 4,946, 778) may be adapted to produce AMG protein or peptide-specific single chain antibodies. An additional embodiment of the invention utilizes the techniques described for the construction of Fab expression libraries (Huse et al., 1989, *Sci-* ence 246, 1275-1281) to allow rapid and easy identification of monoclonal Fab fragments with the desired specificity.

Antibody fragments which contain the idiotype of the molecule can be generated by known techniques. For example, such fragments include but are not limited to: the $F(ab')_2$ fragment which can be produced by pepsin digestion of the antibody molecule; the Fab' fragments which can be generated by reducing the disulfide bridges of the $F(ab')_2$ fragment, the Fab fragments which can be generated by treating the antibody molecule with papain and a reducing agent.

5.4. Screening Methods

The present invention provides for methods of screening for agents that counteract the effect of HIV infection on astrocytes. Such methods comprise culturing early passage human fetal astrocytes, contacting the cultured astrocytes with HIV-1, further contacting the cultured astrocytes with an agent that is a candidate for counteracting the effects of HIV-1 infection on astrocytes, and monitoring the effect of the candidate agent on the expression of AEGs or ASGs, and comparing the level of expression of the AEGs, or ASGs in the presence and absence of the candidate agent, wherein an agent that counteracts the effects of HIV-1 expression in astrocytes is one that prevents the enhancement of expression of an AEG, or prevents the suppression of expression of an ASG.

According to such methods, the effect of a test agent on the expression of an AMG is monitored. Such methods are typically carried out in vitro using cultured astrocytes. An AMG is defined by a modulated level of expression, either upregulation or downregulation, or an altered temporal expression pattern, associated with HIV-1 infection and/or exposure to HIV-gp120; however, it may be found that other viruses or viral proteins may produce similar reductions in AMGs originally defined by an HIV-1/gp120 system, in which case such viruses or proteins may be used in the screening methods of the invention. For example, it may be preferable to use a crippled virus (e.g. incapable of proper packaging) rather than a wild-type virus to lessen the risks of infection.

According to the screening methods of the invention, a test agent may be evaluated for its ability to either prevent or decrease the enhancement of AEG expression associated with such viral infection or viral protein exposure, or to prevent or increase the reduction of ASG expression associated with such viral infection or viral protein exposure. The test agent may be introduced into an cell culture either prior to, concurrent with, or subsequent to introduction of virus or viral protein. The effect of the test agent on AMG expression may be monitored, for example, by measuring RNA and/or protein levels, using techniques known in the art. In specific, non-limiting embodiments of the invention, the AEGs to be monitored are AEG-1 through AEG-15, the ASGs to be monitored are ASG-1 through ASG-10. RNA levels of AEGs, or ASGs may be determined by Northern analysis or PCR. Protein levels may be determined by Western Blot Analysis using anti-AEG, or anti-ASG polyclonal or monoclonal antibodies. Similarly, other AMGs described herein may be monitored using similar methods.

Other screening methods of the invention are based on the discovery that enhanced AEG-1 expression decreases glutamate transport. Accordingly, the methods set forth above may be modified such that instead of measuring AEG levels directly, they may be measured indirectly, by determining the glutamate transport activity of the culture. For example, the amount of glutamate uptake of the astrocytes may be measured, for example, using detectably labeled glutamate. Intracellular levels of glutamate or the level of glutamate in the culture medium may be determined.

In related embodiments, the invention provides for screening methods for the identification of agents which increase glutamate transport. Such methods have the same steps as those intended to identify agents for treating or preventing HAD whereby either the expression level of AEG-1 or the glutamate transport activity is measured. Agents which increase glutamate transport may be useful in treating or preventing a variety of neurological conditions, including HAD, cerebral ischemia, amyotrophic lateral sclerosis, epilepsy and Alzheimer's disease.

In still other embodiments, the present invention provides for cell cultures and transgenic animals which overexpress an AEG or underexpress an ASG, thereby producing a model system for diseases associated with astrocyte pathology.

In the case of AEGs, the AEG may be placed under the control of a strong promoter. In particular non-limiting embodiments, the promoter may be inducible. Examples of suitable promoters are set forth in Section 5.1. The promoters are desirably active in astrocytes. In specific non-limiting embodiments of the invention, cells in culture or in a transgenic animal are engineered to contain AEG-1 under the control of a heterologous promoter, so that AEG-1 may be overexpressed and/or inducibly expressed. Such cells or animals may be used as model systems for study in HAD or other neurological conditions associated with AEG-1 overexpression, and may be used to identify agents which may treat or prevent such conditions.

In the case of ASGs, the expression of the ASG may be reduced in either the cell culture or transgenic animal model systems using an antisense construct or a ribozyme directed against the ASG mRNA sequence. Alternatively, triplex technology may also be used to reduce transcription of the ASG gene. ASG knock-out or knock-out/knock-in models may also be produced in which the ASG is disrupted by insertion of heterologous DNA.

Such cells or animals may be used as model systems for study in HAD or other neurological conditions associated with modulated expression of AMGs, and may be used to identify agents which may treat or prevent such conditions.

5.5. Methods of Diagnosis and Treatment

The present invention further provides for methods of diagnosis and treatment of a disorder associated with a change in expression of one or more AMG. In one set of embodiments, the invention provides for methods of diagnosing HIV-1 infection and/or HAD in a subject comprising determining whether the level of an AEG is elevated in an astrocyte of the subject. The level of expression may be determined directly, for example using a brain biopsy, or indirectly, for example, by determining the level of an AEG protein or a metabolic product thereof in a body fluid of the subject, such as in serum or in cerebrospinal fluid. Metabolic imaging techniques analogous to PET scan may also be employed. An indirect metabolic product may also be used to detect increased AEG expression; for example, since AEG-1 decreases glutamate transport, an increase in cerebrospinal fluid levels of glutamate is consistent with enhanced AEG-1 expression.

In a second set of embodiments, the invention provides for methods of diagnosing HIV-1 infection and/or HAD in a subject comprising determining whether the level of an ASG gene is reduced in an astrocyte of the subject. The level of expression may be determined directly, for example using a brain biopsy, or indirectly, for example, by determining the level of an ASG protein or a metabolic product thereof in a body fluid of the subject, such as in serum or in cerebrospinal fluid. Metabolic imaging techniques analogous to PET scan may also be employed.

An indirect metabolic product may also be used to detect decreased ASG expression.

Further, in view of the association between increased AEG-1 expression and decreased glutamate transport, the present invention provides for methods of decreasing extracellular glutamate levels, and hence treating or preventing conditions associated with neuronal glutamate toxicity, comprising antagonizing the effects of AEG-1. In one non-limiting embodiment, AEG-1 may be antagonized by inhibiting its expression using antisense RNA molecules complementary to all or a portion of AEG-1 nucleic acid, for instance having the sequence set forth as SEQ ID NO:1. The design of antisense molecules, including oligonucleotides, is known in the art. Conditions which may be treated or prevented in this manner include but are not limited to cerebral ischemia, amyotrophic lateral sclerosis, and Alzheimer's disease. The present invention further provides for the treatment or prevention of HAD by antagonizing the effects of AEG-1, for example using antisense molecules as set forth supra.

The present invention further provides for the treatment or prevention of HAD by overexpression of ASGs, for example by using vectors of various forms, both virus-based and non-virus-based, to introduce additional expressible copies of ASGs into astrocytes. Examples of such vectors for the expression of ASGs have been set forth supra.

6. EXAMPLE

6.1. Materials and Methods

Human fetal astrocvtes, other cells and cell culture conditions. Fetal astrocytes- were isolated from second trimester (gestational age 16-19 wk) human fetal brains obtained from elective abortions in fill compliance with NIH guidelines, as previously described (Bencheikh et al., 1999, *J. Neurovirol.* 5, 115-124; Canki et al., 2001, *J. Virol.* 75, 7925-7933). Highly homogenous preparations of astrocytes were obtained using high-density culture conditions in the absence of growth factors in F12 Dulbecco's Modified Eagle Medium (GIBCO-BRL, Gaithersburg, Md.) containing 10% fetal bovine serum (FBS), penicillin, streptomycin, and gentamycin. Cells were maintained in this medium at $2-5 \times 10^4$ cells/cm$^2$ and subcultured weekly up to six times. For each experiment a single batch of astrocytes of similar gestational age and passage was used. Cultures were regularly monitored for expression of the astrocytic marker glial fibrillary acidic protein (GFAP) and either HAM56 or CD68 to identify cells of monocyte/macrophage lineage. Only cultures that contained ≧99% GFAP positive astrocytes and rare or no detectable HAM56- or CD68-positive cells were used in these experiments (Canki et al., 2001, *J. Virol.* 75, 7925-7933). Other cells used in this study were the human embryonal-kidney epithelial cell line 293T (Graham et al., 1977, *J. Gen. Virol.* 36, 59-72), used for HIV-1 propagation, and MAGI cells, a derivative of HeLa carrying the β-gal gene under the control of HIV-1 LTR and expressing HIV-1 receptors (Kimpton & Emerman, 1992, *J. Virol.* 66, 2232-2239), used as indicator cells for HIV-1 titration. Both cell lines were cultured in 90% DMEM/10% FBS supplemented with antibiotics and, for MAGI cells, 0.2 mg/ml G-418. Culture media and cells were tested for mycoplasma contamination using the Mycoplasma PCR ELISA kit (Roche Molecular Biochemicals, Indianapolis, Ind.) and found to be negative.

HIV-1 propagation. The HIV-1 strain used in this work was NL4-3, a prototypical X4-tropic laboratory clone of HIV-1 that expresses all known HIV-1 proteins (Adachi et al., 1986, *J. Virol.* 59, 284-91). Virus propagation was initiated by transfection of 15 μg of NL4-3 DNA into $1.5 \times 10^6$ 293T cells as previously described (Bencheikh et al., 1999, *J. Neurovirol.* 5, 115-124). Culture supernatants were harvested 72 h after transfection, filtered through a 0.45 μm Millipore filters, and stored at −80° C. until use. Cell-free viral stock was tested for HIV-1 p24 core antigen content by ELISA using HIV-1 Ag kit according to the manufacturer's instructions (Coulter, Hialeah, Fla.) and for titers of infectious virus by multinuclear activation of a β-galactosidase indicator (MAGI) assay (Kimpton & Emerman, 1992, *J. Virol.* 66, 2232-2239). Culture supernatants contained 1-2 μg/ml of viral p24 protein and $1-2 \times 10^6$ infectious units (L.U.) per ml. In our experience, a MOI of one for CD4-positive T cells is approximately 1 μg of viral p24 per cell (Dewhurst et al., 1987, *J. Virol.* 61, 3774-3782; Canki et al., 2001, *J. Virol.* 75, 7925-7933)). Virus stocks were also tested for mycoplasma contamination as described above and for endotoxin using the E-TOXATE kit (Limulus Amebocyte Lysate, Sigma, St. Louis, Mo.), and found to be negative in both tests.

HIV-1 infection of astrocvtes with HIV-1 or exposure of the cells to gp120, and preparation of samples for cellular RNA analysis. Confluent cultures of human fetal astrocytes in 225 cm$^2$ culture flasks were exposed to HIV-1 in 10 ml of medium at 1 pg p24 per cell for 2 h at 37° C., washed 3 times in warm PBS, and cultured in astrocyte culture medium as described. Control astrocytes were treated as described above but without HIV-1. At 6 h, 12 h, 24 h, 3 d and 7 d after infection, culture supernatants were removed, and control and infected cells were washed 3 times in PBS and solubilized by addition of 10 ml of 4M guanidine isothiocyanate directly to culture flasks. Cell lysates were stored at −80° C. until further use. To insure preparation of sufficient amount of RNA for subsequent subtractive hybridization, astrocyte cultures and HIV-1 infections were scaled up to approximately $1 \times 10^8$ cells per time point (infected or control cells); the RNA yield was 5-10 μg per 10$^6$ cells. Infection of astrocytes with HIV-1 was verified by testing the levels of HIV-1 p24 antigen in culture supernatants by p24 ELISA as described previously (Bencheikh et al., 1999, *J. Neurovirol.* 5, 115-124; Canki et al., 2001, *J. Virol.* 75, 7925-7933). gp120 used for these experiments was a full-length, glycosylated protein from HIV-1mN produced from baculovirus vector and purified by ImmunoDiagnostics, and provided through the AIDS Research and Reference Reagent Program (Rockville, Md.). For gp120 treatment of astrocytes, large-scale cultures of cells prepared as described above were treated with gp120 at 1 nM in 10 ml medium for 2 h, and cells were washed, cultured, and extracted for RNA isolation as described for HIV-1 infection.

RNA isolation and Northern blot analysis. Uninfected, HIV-1 infected and exposed gp120 astrocytes were treated with 4M-guanidinium and total RNA was isolated by the guanidinium/phenol procedure and analyzed by Northern blotting as described previously (Jiang & Fisher, 1993, *Mol. Cell. Different.* 1, 285-299; Kang et al., 1998, *Proc. Natl. Acad. Sci. U.S.A.* 95, 13788-13793; Kang et al., 2001, *Gene* 267, 233-242). Northern blots were quantitated by densitometric analysis using a Molecular Dynamics densitometer (Sunnyvale, Calif.). Relative expression of the different AEGs or ASGs versus GAPDH expression was determined at different time points for HIV-1 infected (H-AEG/H-GAPDH or H-ASG/H-GAPDH), gp120-treated (G-AEG/G-GAPDH or G-ASG/G-GAPDH) and control uninfected cultures (C-AEG/C-GAPDH or C-ASG/C-GAPDH). Relative fold-change in expression of each AMG at 6 h, 12 h, 24 h, 3 d and 7 d was then determined for each condition by dividing H-AEG/H-GAPDH or H-ASG/H-GAPDH by C-ASG/C-GAPDH or C-ASG/C-GAPDH, respectively, to generate fold HIV modulation; or by dividing G-AEG/G-GAPDH or G-ASG/G-GAPDH by C-AEG/C-GAPDH or C-ASG/C-GAPDH to generate fold gp 120 modulation. Poly(A) RNA was purified using Oligo(dT) cellulose columns (GIBCO BRL).

AEG Protein Analysis by Immunoblotting. Analysis of AEG protein products in astrocytes was determined by immunoblotting. Astrocytes were infected with HIV-1 at an M.O.I. of 1, washed, and cultured in parallel with uninfected controls as described above. At the designated times, cells were counted and lysed in a buffer containing 1% Triton X-100, 0.1% SDS, 1% sodium deoxycholate, 5 mM iodoacetamide, 0.2 U/ml phenylmethylsulfonyl fluoride; cell lysates corresponding to equivalent number of cells were resolved by SDS-PAGE on 4-15% polyacrylamide ready gels (Bio-Rad, Hercules, Calif.) and transferred onto a 0.2 μm Trans-Blot nitrocellulose membrane (Bio-Rad). The membranes were incubated in 5% (w/v) skim milk in T-PBS (0.1% polyoxyethyline-sorbitan monolaurate in phosphate buffered saline) and then stained with the indicated primary antibodies followed by horseradish peroxidase-conjugated second antibody. Protein bands were visualized on x-ray film after luminescence reaction using an ECL kit (Amersham, Arlington, Ill.). Samples were standardized by their α-tubulin content prior to final evaluations. Antibodies used were: rabbit polyclonal anti-fibronectin antibody (Abcam, Cambridge, UK), monoclonal anti-α-actinin (Sigma), and monoclonal anti-β-tubulin (Sigma).

Primer design for RaSH procedure. The sequences of oligonucleotides that were used are as follows: XDPN-18 CTGATCACTCGAGAGATC (SEQ ID NO:5), XDPN-14 CTGATCACTCGAGA (SEQ ID NO:6), XDPN-12 GATCTCTCGAGT (SEQ ID NO:7). The adapters formed from the two sets of oligonucleotides contained an XhoI recognition site.

Preparation of PCR-based cDNA libraries used in RaSH procedure. To clone AEG cDNAs expressed at elevated levels in early passage human fetal astrocytes, 1 μg of poly(A) RNA from temporally spaced (6 h, 12 h, 24 h, and 3 d and 7 d) uninfected astrocytes (driver) or temporally spaced (6 h, 12 h, 24 h, and 3 d and 7 d) HIV-1 infected astrocytes (tester) prepared as described above was used for double-stranded cDNA synthesis using standard protocols (Gubler & Hoffman, 1983, Gene 25, 263-269). To clone ASG cDNAs expressed at reduced levels in early passage human fetal astrocytes, 1 μg of poly(A) RNA from temporally spaced (6 h, 12 h, 24 h, and 3 d and 7 d) HIV-1-infected astrocytes (driver) or temporally spaced (6 h, 12 h, 24 h, and 3 d and 7 d) mock-infected astrocytes (tester) prepared as described above was used for double-stranded cDNA synthesis using standard protocols (Gubler & Hoffinan, 1983, Gene 25, 263-269).

The resulting cDNAs were digested with DpnII (New England Biolab, Beverly, Mass.) at 37° C. for 3 h followed by phenol/chloroform extraction and ethanol precipitation. The digested cDNAs were mixed with primers XDPN-14/XDPN-12 (final concentration 20 μM) in 30 μl of 1× ligation buffer (GIBCO BRL), heated at 55° C. for 1 min, and cooled down to 14° C. within 1 h. After adding 3 μl of T4 ligase (5 U/μl) (GIBCO BRL) to the mixtures individually, ligation was carried out at 14° C overnight. The mixtures were diluted to 100 μl with TE buffer (pH 7.0), and at least 40 μl of the mixtures were used for PCR amplification. The PCR mixtures were set up as follows: 1 μl of the cDNA mixture, 10 μl 10× PCR buffer, 1 mM MgCl$_2$, 0.4 mM dNTPs, 1 μM XDPN-18, and 1 U Taq polymerase (GIBCO BRL). The parameters for PCR were one cycle for 5 min at 72° C. followed by 25 cycles for 1 min at 94° C., 1 min at 55° C., 1 min at 72° C. preceded by one cycle for 3 min at 72° C. The PCR products were pooled and purified using Centricon columns (Amicon, Bedford, Mass.). Ten μg of the tester PCR products were digested with XhoI followed by phenol/chloroform extraction and ethanol precipitation.

Subtraction hybridization and generation of subtracted libraries. One hundred ng of the tester cDNA were mixed with 3 μg of the driver cDNA in 10 μl of a hybridization solution (0.5 M NaCl, 50 mM Tris pH 7.5, 0.2% SDS, 40% formamide), and after boiling for 5 min, incubated at 42° C. for 48 h. The hybridization mixture was phenol/chloroform extracted, ethanol precipitated, and dissolved in 20 μl of TE buffer. One μl of the mixture was ligated with 1 μg of XhoI-digested, CIP-treated pCRII plasmids, overnight at 14° C., and transformed into Shot-1 bacteria.

Colony screening. Bacterial colonies were randomly picked and PCR amplified. The PCR products were blotted onto filters and reverse Northern blotting was performed to identify cDNAs displaying differential expression in HIV-1 infected versus uninfected early passage human fetal astrocytes (Kang et al., 1998, Proc. Natl. Acad. Sci. U.S.A. 95, 13788-13793; Huang et al., 1999, Gene 236, 125-131; Jiang et al., 2000, Proc. Natl. Acad. Sci. U.S.A. 97, 12684-12689). cDNAs displaying elevated expression in HIV-1 infected fetal astrocytes versus uninfected fetal astrocytes were designated AEG with a clone number of AEG-1 to AEG-15, while cDNAs displaying reduced expression in HIV-1 infected fetal astrocytes versus uninfected fetal astrocytes were designated ASG with a clone number of ASG-1 to ASG-10. Appropriate expression of the AMG clones identified by reverse Northern blotting was confirmed by Northern blotting. The sequences of these clones were determined using automated cycle sequencing at the DNA facility of Columbia University.

6.2. Results

Infection of human astrocytes with HIV-1 and cloning of the AMGs using the RaSH approach. Human fetal astrocytes were cultured and infected with HIV-1 (NL4-3 clone) as previously described (Bencheikh et al., 1999, J. Neurovirol. 5, 115-124; Canki et al, 2001, J. Virol. 75, 7925-7933). Mock-infected cells were cultured and handled similarly in parallel as a control. HIV-1 infection of astrocytes alters gene expression and cell function (He et al., 1997, Proc. Natl. Acad. Sci. U.S.A. 94, 3954-3959; Kort, 1998, AIDS Res. Hum. Retroviruses 14, 1329-1339). To define the repertoire of genes modified as a consequence of infection of early passage fetal astrocytes with HIV-1, the efficient and rapid cloning approach RaSH was used (Jiang et al., 2000, Proc. Natl. Acad. Sci. U.S.A. 97, 12684-12689; Kang et al., 2001, Gene 267, 233-242; Siumn et al., 2001, Gene 269, 93-101). A schematic of this approach as applied to this fetal astrocyte model and HIV-1 infection is shown in FIGS. 1 and 2. For the current study, human fetal astrocytes were cultured and infected with HIV-1 as previously described (Bencheikh et al., 1999, *J. Neurovirol.* 5, 115-124; Canki et al., 2001, *J. Virol.* 75, 7925-7933) and pooled RNAs (6 h, 12 h, 24 h, and 3 d and 7 d) extracted from uninfected and HIV-1 infected early passage fetal astrocytes cultured in parallel were used in RASH to identify cellular genes displaying modulated expression (AMGs) as a function of HIV-1 infection. HIV-1 infection of astrocytes was confirmed by following the levels of HIV-1 p24 core antigen in culture supernatants (FIG. 3A). Consistent with previous results from this and other laboratories (Tomatore et al., 1991, *J. Virol.* 65, 6094-6100; Canki et al., 2001, *J. Virol.* 75, 7925-7933), HIV-1 production by these cells peaked 3-4 d after infection at about 600 µg p24/ml and it declined thereafter (FIG. 3A).

In general, the RaSH procedure followed that described for identification of cellular genes displaying elevated expression in astrocytes, as shown in FIG. 1. For the identification of cellular genes displaying reduced expression in infected astrocytes, the tester and driver libraries were reversed, as shown schematically in FIG. 2. The cDNA libraries were prepared by synthesizing double-stranded cDNAs, digesting the cDNAs into small fragments with the restriction enzyme DpnII, ligating the fragments to adapters and amplifying by PCR. The DpnII-based RaSH approach was previously shown to generate fragments of at least 256 bp in size (Jiang et al., 2000, *Proc. Natl. Acad. Sci. USA* 97, 12684-12689). Subtraction hybridization was then performed by incubating the tester and driver PCR fragments without further PCR amplification.

Selection of subtracted cDNAs for the identification of AEGs was achieved by matching the ends of the cDNA fragments to the ends of the plasmid vectors during ligation and construction of subtracted libraries (FIG. 1). Selection of subtracted cDNAs for the identification of ASGs was achieved by ligation of the common XhoI restriction sites at the termini of the cDNA fragments and the plasmid vectors (FIG. 2). Initial screening of a large number of clones representing differential expression of cellular genes was accomplished by reverse Northern hybridization, followed by Northern blotting to confirm true differential expression of genes in infected versus control cells (Kang et al., 1998, *Proc. Natl. Acad. Sci. U.S.A.* 95, 13788-13793; Huang et al., 1999, *Gene* 236, 125-131). Previous studies document a high degree of conformity (~89%) between reverse Northern and Northern expression of RaSH-derived ESTs (Jiang et al., 2000, *Proc. Natl. Acad. Sci. U.S.A.* 97, 12684-12689; Simm et al., 2001, *Gene* 269, 93-101).

Using this approach, 15 distinct AEGs displaying enhanced expression (FIG. 4) and 10 distinct ASGs displaying reduced expression (FIG. 5) following HIV-1 infection were identified by reverse Northern blotting. Of the AEGs, thirteen were previously identified AEGs and two were unknown AEGs (AEG-1 and AEG-11) not reported in current databases (Table 1). RaSH identified AEG-1 (novel) in four independent analyses and AEG-2 (G-binding protein) (Beals et al., 1987, *Proc. Natl. Acad. Sci. U.S.A.* 84, 7886-7890) in two independent analyses, whereas the remaining AEGs represented single cloning events. Of the ASGs, nine were previously identified ASGs and one was an unknown ASG (ASG-1). ASG-4, -6, -7, and -9 were isolated in two independent RaSH analyses, whereas the remaining ASGs represented single cloning events (Table 2). Since only about 20% of the DpnII RaSH subtracted library was screened, it is estimated that this library may contain more than 75 distinct differentially expressed AEGs and 50 or more distinct differentially expressed ASGs.

Sequence analysis of the RaSH-derived ESTs revealed nine previously identified ASGs and one unknown ASG, designated ASG-1 (novel), not reported in current databases (Table 1). Among the known ASG products are proteins involved in cell movement and cell differentiation (ASG-3, platelet-endothelial tetraspan antigen 3 (PETA-3); ASG-5, neuronatin; and ASG-6, a neuroendocrine differentiation factor), as well as intracellular regulators of signal transduction and gene expression (ASG-4, a guanine-nucleotide releasing protein C3 G; ASG-7, cysteine/glycine rich protein 1 (CSRP1); and ASG-10, signal recognition particle 9 (SRP9).

In contrast, the AEGs included a wider range of genes, including AEG-2 (G-binding protein), AEG-3 (GA 17 protein) (Ryo et al., 2000, *AIDS Res. Hum. Retroviruses* 16, 995-1005), AEG-4 (unr/NRU) (Jeffers et al., 1990, *Nucleic Acids Res.* 18, 4891-4899; Boussadia et al., 1993, *Biochim. Biophys. Acta* 1172, 64-72), AEG-5 (hGNT-IV-H) (Furukawa et al., 1999, *J. Hum. Genet.* 44, 397-401), AEG-6 (fibronectin), AEG-7 (human CTL2) (O'Regan et al., 2000, *Proc. Natl. Acad. Sci. U.S.A.* 97, 1835-1840), AEG-8 (acidic ribosomal phosphoprotein) (Rich & Stietz, 1987, *Mol. Cell Biol.* 7, 4065-4074), AEG-9 (calnexin) (Honore et al., 1994, *Electrophoresis* 15, 482-490; Rubio & Wenthold, 1999, *J. Neurochem.* 73, 942-948; Shi et al., 2001, *Cell* 105, 331-342), AEG-10 (autotaxin) (Stracke et al., 1994, *J. Biol. Chem.* 267, 2524-2529; Kawagoe et al., 1997, *Cancer Res.* 57, 2516-2521), AEG-12 (thymosin β-4) (Gondo et al., 1987, *J. Immunol.* 139, 3840-3848), AEG-13 (human non-muscle α-actinin) (Youssoufian et al., 1990, *Am. J. Hum. Genet.* 47, 62-71), AEG-14 (Schneider et al., 1988, *Cell* 54, 787-793; Gonos, 1998, *Ann. N.Y. Acad. Sci.* 851, 466-469; Prieto et al., 1999, *Brain Res.* 816, 646-661) and AEG-15 (PGK-1) (Michelson et al., 1983, *Proc. Natl. Acad. Sci. USA* 80, 472-476; Tsukada et al., 1991, *J. Gerontol.* 46, B213-B216).

Expression analysis and characterization of AMGs. The differential expression of the RaSH-derived AMGs was confirmed by Northern blot analyses, shown in FIGS. 6 through 8 for AEGs and FIGS. 9 through 11 for the ASGs. The results of densitometry analyses of ASG expression are shown in FIG. 12. RNAs were isolated after 6 h, 12 h, 24 h, and 3 d and 7 d from uninfected, HIV-1 infected, and HIV-1 glycoprotein (gp 120)-treated early passage human fetal astrocytes. gp120 treatrnent was included in this analysis because gp120 alone (without infection with intact HIV-1) induces marked functional and gene-expression changes in human astrocytes (Schneider-Schaulies et al., 1992; Benos et al., 1994b; He et al., 1997; ). RNA levels were quantitated by Northern blotting, first by probing with a random-primed [$^{32}$P]-labeled ASG or ASG cDNAs, followed by stripping of the blot and reprobing with a probe for the transcript of the human housekeeping enzyme, glyceraldehyde-3-phosphate dehydrogenase (gapdh). After autoradiography, relative hybridization intensity was determined by densitometry comparisons of AEG/gadph or ASG/gadph for the various temporal uninfected samples relative to HIV-1 infected or gp 120-treated normalized (AEG/gadph or ASG/gadph) RNA samples, as described above in the Materials and Methods. The experiments and analyses were repeated two to three times using different preparations of astrocytes and virus or gp 120 and qualitatively similar results were observed.

Compared to their expression in control cells, an ~1.5- to ~4.5-fold temporal increase in expression of the various AEGs was apparent following HIV-1 infection and an ~1.5- to ~3.2-fold temporal increase was seen following gp120 treatment (Table 1; see below). The expression of specific ASGs was reduced at defined time-points up to ~5.1-fold by HIV-1 infection and up to ~4.2-fold following gp120 treatment (Table 2 and FIG. 12).

In general, the temporal pattern and magnitude of enhanced AEG expression was similar in cells infected with HIV-1 or treated with gp 120. However, expression of AEG-2 (G-binding protein), AEG-5 (hGNT-IV-H) (Furukawa et al., 1999), AEG-7 (human CTL2) (O'Regan et al., 2000), AEG-8 (acidic ribosomal phosphoprotein) (Rich & Stietz, 1987) and AEG-15 (PGK-1) (Michelson et al., 1983, *Proc. Natl. Acad. Sci. USA* 80, 472-476; Tsukada et al., 1991, *J. Gerontol.* 46, B213-B216) was elevated in fetal astrocyte cultures more rapidly following HIV-1 infection than gp120 treatment (FIGS. 6 through 8). AEG-2 (G-binding protein), AEG-5 (hGNT-IV-H) and AEG-7 (human CTL2) expression was elevated by 3 d post-infection with HIV-1, whereas enhanced expression of these genes was not apparent until 7 d after gp120 treatment. In the case of AEG-8 (acidic ribosomal phosphoprotein) and AEG-15 (PGK-1) increased expression was apparent by 24 h following infection with HIV-1 and by 3 d following gp120 treatment. Quantitative differences in enhancement were also apparent with HIV-1 causing a greater increase than gp120 in the case of AEG-2 (G-binding protein), AEG-3 (GA17 protein) (Ryo et al., 2000), AEG-7 (human CTL2), AEG-10 (autotaxin) (Stracke et al., 1994, *J. Biol. Chem.* 267, 2524-2529; Kawagoe et al., 1997, *Cancer Res.* 57, 2516-21) and AEG-13 (human non-muscle a-actinin) (Youssoufian et al., 1990, *Am. J. Hum. Genet.* 47, 62-72).

AEG-3 (GA17 protein), AEG-11 (novel) and AEG-13 (human non-muscle α-actinin) appear to be early response genes, which are elevated by 6 h after infection with HIV-1 or treatment with gp120 (FIGS. 6 through 8). In contrast, AEG-1 (novel), AEG-2 (G-binding protein), AEG-4 (unr/NRU) (Jeffers et al., 1990, *Nucl. Acids. Res.* 18, 4891-4899; Boussadia et al., 1993, *Biochim. Biophys. Acta* 1172, 64-72), AEG-5 (hGnT-IV-H), AEG-7 (human CTL2), AEG-8 (acidic ribosomal phosphoprotein), AEG-9 (calnexin) (Honore et al., 1994, *Electrophoresis* 15, 482-490; Rubio & Wenthold, 1999, *J. Neurochem.* 73, 942-948; Shi et al., 2001), *Cell* 105, 331-342, AEG-10 (autotaxin) and AEG-(Schneider et al., 1988, *Cell* 54, 787-793; Gonos, 1998, *Ann. N.Y. Acad. Sci.* 851, 466-469; Prieto et al., 1999, *Brain Res.* 816, 646-661), represent late response genes that display elevated expression by 3 to 7 d post-treatment (FIGS. 6 through 8). Specific AEGs had unique temporal expression patterns. In the case of AEG-6 (fibronectin) (Niquet et al., 1994, *Neurosci. Lett.* 180, 13-16), elevated expression was predominantly detected 24 h after exposure to HIV-1 or gp120 (FIG. 7). In the case of AEG-12 (thymosin β-4) (Gondo et al., 1987, *J. Immunol.* 139, 3840-3848), enhanced activity was observed following HIV-1 and gp120 treatment for 24 h and 7 d, whereas no enhancement was apparent at 6 h or 3 d (FIG. 8). While most of the AEGs hybridized with a single MRNA species, AEG-11 (novel) and AEG-13 (human non-muscle α-actinin) hybridized with two separate mRNA species, which may reflect alternate processing of the same gene.

Figure 13:
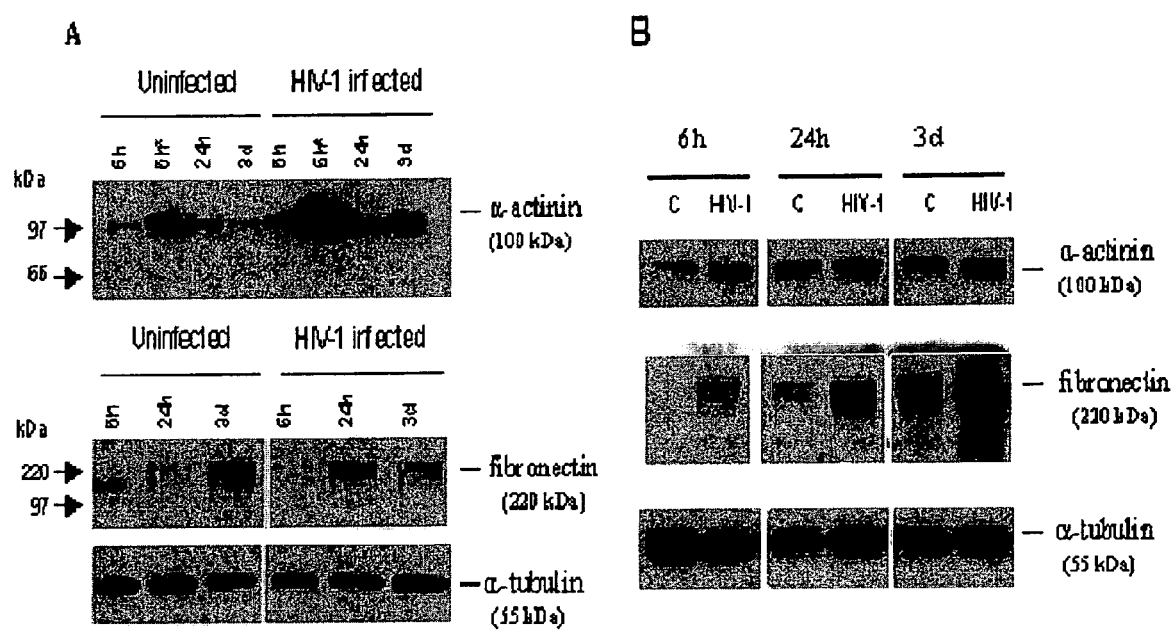

HIV-1 infection and gp120 treatment of early passage fetal astrocytes enhances fibronectin and α-actinin protein expression. To determine if elevated AEG mRNA correlated with enhanced protein expression, we obtained commercially available antibodies to fibronectin (AEG-6), calnexin (AEG-9) and human non-muscle α-actinin (AEG-13) and tested expression of these proteins in HIV-1 infected and control astrocytes by Western blotting. The results of analyses of fibronectin and α-actinin protein expression in two independently derived primary human fetal astrocyte cultures are shown in FIG. 13. Although fibronectin (AEG-6) levels were elevated in both astrocyte cultures following HIV-1 infection, the kinetics of increase was different for the two different astrocyte cultures. In the cultures analyzed in FIG. 13A, enhancement was only apparent after 24 h, which correlated with a similar increase in AEG-6 mRNA in these cells following HIV-1 infection (FIG. 7). However, in the astrocyte cultures analyzed in FIG. 13B, increases in fibronectin were apparent after 6 h, 24 h and 3d. Similarly, α-actinin (AEG-13) levels were elevated after HIV-1 infection only at 6 h in the astrocytes in FIG. 13A, whereas an increase at 6 h and a small increase at 24 h were apparent in the astrocytes in FIG. 13B. The difference in the temporal kinetics of expression between these two cultures following HIV-1 infection may reflect cellular heterogeneity or the growth status of these astrocyte cultures. However, since the cultures in FIG. 13B were not examined for fibronectin or α-actinin mRNA it is not known if mRNA synthesis displayed similar kinetic changes in these cells following HIV-1 infection. Calnexin (AEG-13) could not be detected in astrocytes under any conditions. Thus, for two of the AEG products, fibronectin (AEG-6) and α-actinin (AEG-13), HIV-1 induced elevations in mRNA expression correlate with increases in their respective protein levels.

Similar to differentially expressed gene products described above for AEGs, the ASGs also display distinct patterns of expression over time in response to HIV-1 infection of astrocytes, again stratifying into early and sustained versus late responders (Table 2, FIGS. 9-11). Six out of the 10 ASGs, (ASG-1, -2, -3, -5, -6, and -9) can be considered late-response genes with changes apparent in their expression only 3 d and 7 d after HIV-1 exposure (FIGS. 9-11). A temporal decrease in expression of ASG-1, -5, and -9 was apparent over the seven days of observation. ASG-4, -7, and -8 were early, sustained response genes whose expression was suppressed within 6-24 h and remained suppressed for the rest of the period of observation (FIGS. 10 and 11). ASG-4, the signal transduction protein C3G, showed an interesting pattern including an increase in expression 6 h after infection followed by decreasing expression relative to control cells from 1 d to 7 d after infection, suggesting several levels of transcriptional control of C3G. ASG-6 reaches a nadir of expression 3 d after infection with HIV-1, followed by a rebound in expression at 7 d. The observation that the extent and time course of perturbation of cellular gene expression by a given agent is specific to the particular transcript examined reproduces the cellular response pattern seen previously in astrocytes (Su et al., 2002, *Oncogene* 21, 3592-3602) and in terminally-differentiated human melanoma cells (Huang et al., 1999, *Gene* 236, 125-131), and in work by others (Corbeil et al., 2001, *Genome Res* 11, 1198-1204), underscoring the generality of this phenomenon and the importance of assessing RNA levels at multiple times after a single stimulus or multiple stimuli.

TABLE 1

General Characteristics of Genes Enhanced in HIV-1-infected and gp120-treated astrocytes (ASGs)

| Gene designation | Maximum upregulation* | | Approx. size of mRNA (kb) | # of Clonal isolates** | Sequence homology |
|---|---|---|---|---|---|
| | HIV-1 infected | gp120 treated | | | |
| AEG-1 | 2.3 (7 d) | 2.7 (7 d) | ~3.0 | 4 | Novel sequence |
| AEG-2 | 4.1 (3 d, 7 d) | 3.0 (3 d) | 1.6 | 2 | Human G-binding protein (coupling protein G(s) alpha-subunit (alpha-S1) (stimulatory regulatory component Gs of adenyl cyclase) |
| AEG-3 | 4.2 (6 h, 24 h) | 2.3 (6 h, 24 h) | 1.7 | 1 | GA17 protein |
| AEG-4 | 2.4 (3 d, 7 d) | 2.5 (3 d, 7 d) | 3.6 | 1 | unr/NRU (gene closely linked to N-ras) |
| AEG-5 | 2.9 (3 d, 7 d) | 1.8 (7 d) | 3.8 | 1 | UDP-N-acetylglucosamine; alpha-1,3-D-mannoside beta-1,4-N-acetylglucosaminyltransferase IV (hGnT-IV-H) |
| AEG-6 | 3.2 (24 h) | 3.2 (24 h) | 7.7 | 1 | Fibronectin |
| AEG-7 | 3.8 (3 d, 7 d) | 2.3 (3 d, 7 d) | 2.8 | 1 | Human CTL2 |
| AEG-8 | 2.0 (24 h, 3 d, 7 d) | 2.0 (3 d, 7 d) | 1.1 | 1 | Acidic ribosomal phosphoprotein |
| AEG-9 | 2.3 (3 d, 7 d) | 2.2 (3 d, 7 d) | 4.0 | 1 | Calnexin (human integral membrane protein) |
| AEG-10 | 4.5 (3 d, 7 d) | 1.6 (3 d, 7 d) | 3.2 | 1 | Autotaxin (phosphodiesterase I) |
| AEG-11 | 2.8 (6 h) | 2.2 (6 h) | ~2.0 & 3.0 | 1 | Novel sequence |
| AEG-12 | 3.2 (24 h, 7 d) | 3.0 (24 h, 7 d) | 0.459 | 1 | Thymosin β4 (interferon-inducible protein) |
| AEG-13 | 3.5 (6 h) | 2.4 (6 h) | ~2.0 & 3.0 | 1 | Human non-muscle α-actinin |
| AEG-14 | 2.8 (3 d, 7 d) | 2.6 (3 d, 7 d) | 2.4 | 1 | gas-6 (growth arrest specific 6 gene) |
| AEG-15 | 2.6 (24 h, 3 d, 7 d) | 2.8 (3 d, 7 d) | 1.6 | 1 | PGK-1 (phosphoglycerate kinase 1) |

*Maximum upregulation of ASG mRNA determined in HIV-1-infected or gp120-treated human fetal astrocytes relative to the same time point in control (untreated) cells. Fold HIV-1 upregulation = C-ASG/C-gapdh divided by H-ASG/H-gapdh. Fold gp120 upregulation = C-ASG/C-gapdh divided by G-ASG/G-gapdh. Time of maximum fold upregulation indicated in parenthesis. h = hour; d = days. When up-regulation was apparent at different time points, maximum upregulation is indicated by underlining. Average fold change from 2 to 3 independent experiments using different primary human fetal astrocyte cultures.
**Reverse Northern blotting identified potential upregulated AEGs. Sequencing indicated that AEG-1 had been cloned two times and AEG-2 had been cloned two times, whereas all of the other AEGs were identified one time in the ~20% of the subtracted library screened by reverse Northern blotting.

TABLE 2

General Characteristics of Genes Suppressed in HIV-1-infected and gp120-treated astrocytes (ASGs)

| Gene designation | Maximum downregulation* | | Approx. size of mRNA (kb) | # of Clonal isolates** | Sequence homology |
|---|---|---|---|---|---|
| | HIV-1 infected | gp120 treated | | | |
| ASG-1 | 4.2 ± 0.5 (7 d)† | 4.8 ± 0.9 (3 d)† | ~4.0 & ~2.0 | 1 | Novel sequence (maps to 11q23) |
| ASG-2 | 3.2 ± 0.5 (3 d)† | 2.1 ± 0.1 (3 d)† | 3.0 & 1.5 | 1 | Human cDNA FLJ10705 (unpublished) (mRNA from NT2 neuronal precursor cell after 2 wk RA induction) |
| ASG-3 | 3.4 ± 0.8 (7 d)† | 3.3 ± 0.4 (7 d)† | 1.5 | 1 | Platelet-endothelial cell tetra-span antigen 3 mRNA (CD151/PETA-3) |
| ASG-4 | 3.5 ± 0.1 (7 d)† | 2.9 ± 0.5 (3 d)† | 4.1 | 2 | Guanine nucleotide-releasing factor, C3G |
| ASG-5 | 4.1 ± 0.1 (7 d)† | 2.9 ± 0.5 (7 d)† | 1.3 | 1 | Neuronatin |
| ASG-6 | 3.2 ± 0.5 (3 d)† | 3.2 ± 0.4 (7 d)† | 3.0, 1.0 & 0.7 | 2 | Neuroendocrine differentiation factor; CGI149 mRNA |
| ASG-7 | 3.5 ± 0.1 (3 d)† | 3.0 ± 0.7 (3 d)† | 1.8 | 2 | Cysteine/glycine rich protein 1 mRNA (CSRP1) |
| ASG-8 | 3.1 ± 0.6 (24 h)† | 3.0 ± 0.1 (24 h)† | ~3.0 & ~1.5 | 1 | MML5 gene |
| ASG-9 | 5.3 ± 0.4 (3 d)† | 3.0 ± 0.7 (7 d)† | 16.5 | 2 | Human mitochondrion (encoding rRNA) |
| ASG-10 | 3.7 ± 0.3 (7 d)† | 1.6 ± 0.2 (7 d) | 2.5 & 1.5 | 1 | Signal recognition particle 9 KD (SRP9KD), human clone 45620 |

*Maximum downregulation of ASG mRNA determined in HIV-1-infected or gp120-treated human fetal astrocytes relative to the same time point in control (untreated) cells. Fold HIV-1 downregulation = C-ASG/C-gapdh divided by H-ASG/H-gapdh. Fold gp120 downregulation = C-ASG/C-gapdh divided by G-ASG/G-gapdh. Time of maximum fold downregulation indicated in parenthesis. Average fold change from 2 independent experiments using different primary human fetal astrocyte cultures ± S.D. Statistical analysis of the gene expression changes between 6 h control and the time point showing maximum change were analyzed using the Student's t-test.
†Indicates that the change in expression is significant ($p < 0.05$). All maximum changes indicated in this table were significant ($p < 0.05$) with the exception of ASG-10 in gp120-treated PHFA at day 7. Qualitatively similar results were obtained in an additional experiment (data not shown).
**Reverse Northern blotting identified potential downregulated ASGs. Sequencing indicated that ASG-4, ASG-6, ASG-7 and ASG-9 had been cloned two times, whereas the rest were identified one time in the ~20% of the subtracted library screened by reverse Northern blotting.

Although the ASG library was constructed on the basis of transcripts from HIV-1 infected astrocytes (FIG. 2), all of the ASGs thus far identified were also suppressed in expression in astrocytes treated with gp120. Neither can the extent of suppression distinguish specific genes modulated by HIV-1 versus gp120-treatment. The maximum suppression observed was induced by HIV-1 in seven of the cases, ASG-3, -4, -5, -6, -7, -9, and -10 but was maximally reduced by gp120 in the remaining three cases, ASG-1, -2, and -8. The only transcript markedly more sensitive to HIV-1 than to gp120 is ASG-5. It is perhaps most interesting that the suppression of gene expression was as sustained in cells exposed to gp120 as in HIV-1-infected cells, for example ASG-8 was suppressed by both agents for seven days of observation. This result is similar to the findings for the AEGs discussed supra. The similar patterns of altered cellular gene expression in infected and gp120-treated astrocytes indicate that intact HIV-1 and gp120 activate similar cellular pathways leading to transcriptional modulation of these genes. It should be noted, however, that since the RaSH library was based on HIV-1 infected cells, these data couldn't identify cellular genes whose expression might be affected by gp120 but not by HIV-1.

Another implication of these results is that some modulatory effects of HIV-1 on cellular gene expression in human astrocytes, like the ones represented by changes in AEG and ASG, are independent of virus replication because they can be reproduced to a significant extent by treatment of cells with recombinant gp120 in the absence of other viral products (FIGS. 6-11). A similar conclusion was reached in a recent study on the regulation of glutamate transporters and glutamate transport in human astrocytes by HIV-1. This conclusion is less surprising if one considers that productive infection of astrocytes by HIV-1 is inefficient and only a small proportion of infected cells, about 1%, express virus products that could possibly affect host cell physiology (Tomatore et al., 1991, *J. Virol.* 65, 6094-6100; Takahashi et al., 1996, *Ann Neurol* 39, 705-711; Bencheikh et al., 1999, *J. Neurovirol.* 5, 115-124). However, the viral effects observed here are "global", that is, they must occur in a majority of cells in order to be detectable. For example, the ~4-fold decline in ASG-7 expression at 24 h after HIV-1 exposure (FIG. 10) can be explained only by a total loss of ASG-7 expression in 75% of affected cells or 75% loss incurred by all the cells in the population.

The replication-independent modulation of cellular gene expression by HIV-1 is likely mediated by efficient viral interaction with surface receptors on astrocytes. Although these cells lack surface CD4, the canonical HIV-1 receptor on T cells and macrophages (Klatzman et al., 1984, *Nature* 312, 767-768; Cheng-Mayer et al., 1987, *Proc. Natl. Acad. Sci. USA* 84, 3526-3530), they do express a high-molecular weight protein of about 260 kDa which was shown to bind gp120 with high affinity (Ma et al., 1994, *J. Virol.* 68, 6824-6828) and which may be responsible for binding intact HIV-1 as well. Astrocytes also express the chemokine receptors CXCR4 and CCR5 (Andjelkovic et al., 1999, *Glia* 28, 225-235; Rezaie et al., 2002, *Glia* 37, 64-75) as well as galactocerebroside (Harouse et al., 1989, *J. Virol.* 63, 2527-2533), all of which can bind HIV-1 envelope. Further studies are needed to determine the identity of the membrane receptors on astrocytes that may mediate the HIV-1 effects on cellular gene expression observed here and in our other studies.

Although RNA transcripts of a single size is apparent in astrocytes after probing with ASG-3, -4, -5, -7 and -9, multiple hybridizing RNA species are apparent in Northern blots after probing astrocyte RNAs with ASG-1, -2, -6, -8 and -10 (FIGS. 9-11). The presence of multiple RNAs may indicate alternative processing of the respective gene resulting in multiple sized transcripts or it could reflect a cloning artifact resulting from two sequences being cloned together in a single RaSH-derived clone. In cases where a decrease is apparent in the multiple RNA species as a consequence of infection with HIV-1 or treatment with gp120, such as ASG-1 and -6, differential processing of a single gene is a more plausible explanation for the different sized mRNAs. However, in the case of ASG-2, -8 and -10, further analysis was performed to determine if chimeric clones have been produced during the RaSH procedure. Use of RaSH in its presently described form highlighted two potential problems that can readily be addressed by minor modifications in the protocol as addressed by Kang et al. (Kang et al., 2002, In: Analysing Gene Expression, Lorkowski S, Cullen P, eds, In press: Wiley-VCH Verlag GmbH, Germany). As indicated above, although the majority of ASG RaSH clones contained single inserts, some clones contained more than one insert that were ligated in tandem (Jiang et al., 2000, *Proc. Natl. Acad. Sci. USA* 97, 12684-12689). Multiple inserts can obscure differential expression in screening procedures, such as reverse Northern hybridization. Moreover, if the gene has not been reported previously, the hybrid molecule can inappropriately serve as a basis for attempting to clone a spurious molecule. Careful consideration, especially with respect to the presence internally of the restriction site used in library construction (DpnII) in the RaSH clone could be used to circumvent this problem. This inspection has been done for the ASGs described in the present study, indicating that those genes hybridizing to multiple transcripts are not chimera genes, i.e., produced as a result of cloning artifacts during the RaSH procedure. Additionally, digestion of a cDNA with a frequent cutter could increase additional redundancy due to cloning different parts of the same gene. Immobilization of the 3'-end by using biotinylated RT primer with a cloning site (e.g., XhoI) and ligation of adapter with another cloning site (BamHI) may prove useful in ameliorating this problem of redundant clone isolation and the isolation of clones containing multiple inserts. This modification in the original protocol will also enhance the cloning efficiency of the differentially expressed insert into the vector (Kang et al., 2002, *Proc. Natl. Acad. Sci. U.S.A.* 99, 637-642).

HIV-1-mediated dysregulation of cellular gene expression in human astrocytes and neuropathogenesis. The major implication of the findings presented here is that HIV-1 has profound, global effects on expression of a broad array of cellular genes in astrocytes, suggesting that this may be one route through which HIV-1 infected astrocytes contribute to HAD. Overall, 25 genes were identified as differentially expressed in astrocytes as a result of HIV-1 exposure, 15 of these were upregulated in their expression (AEGs) and 10 suppressed (ASGs). Based on the size of the RaSH-derived EST libraries utilized in these studies, the number of differentially expressed genes in this system may exceed 100. The magnitude of this HIV-1 effect on astrocyte biology is more remarkable as it occurs despite relatively inefficient viral expression in these cells (Tomatore et al., 1991, *J. Virol.* 65, 6094-6100; Canki et al., 2001, *J. Virol.* 75, 7925-7933; Su et al., 2002, *Oncogene* 21, 3592-3602) and it can be reproduced by treatment of astrocytes with isolated HIV-1 envelope glycoprotein (FIG. 12). As shown by recent gene array and RaSH analyses, HIV-1 also exerts profound effects on cellular gene expression during infection of T lymphocytes (Nye & Pinching, 1990, *AIDS* 4, 41-45; Shahabuddin et al., 1994, *AIDS Res. Hum. Retroviruses* 10, 1525-1529; Swingler et al., 1999, *Nat Med* 9, 997-103; Geiss et al., 2000, *Virology* 266, 8-16; Corbeil et al., 2001, *Genome Res* 11, 1198-1204; Simm et al., 2001, *Gene* 269, 93-101). Notably, in the study of Corbeil et al. (Corbeil et al., 2001, *Genome Res* 11, 1198-1204), HIV-1 infection of CEM cells was associated with a 30% decline in overall cellular RNA expression, replacement of cellular RNA by viral transcripts, and increased expression of proapoptotic genes and selected caspases; these molecular changes are consistent with the known cytopathic course of HIV-1 infection in T cells that culminates in cell death. In contrast, primary astrocytes are not killed by HIV-1 infection in vitro (Tomatore et al., 1991, *J. Virol.* 65, 6094-6100; (Bencheikh et al., 1999, *J. Neurovirol.* 5, 115-124) and the major morphological change observed in astrocytes during HIV-1 infection in vivo is gliosis (Budka, 1991, *Brain Pathol.* 1, 163-175; Sharer, 1992, *J. Neuropath. Exp. Neur.* 51, 3-11), which represents activation and possible expansion of the glial tissue. These findings lend themselves to an interpretation of the current findings as indicating that exposure of astrocytes to HIV-1 or gp120 may induce long-lasting effects on cell physiology and functions rather than affecting cell viability, as with other HIV-1 host cells. Some of these functions, such as maintenance of ionic equilibrium in the synapse and transport of the neurotransmitter L-glutamate, impact neurons directly and their impairment has been shown to cause neurotoxicity (Choi, 1988; *Neuron* 1, 623-634; Maragakis & Rothstein, 2001, *Arch. Neurol.,* 58, 365-370). Recent data also indicate that astrocytes are a critical functional component of the synapse and play a role in signal transmission ((Iino et al., 2001, *Science* 292, 926-929; Oliet et al., 2001, *Science* 292, 923-926; Beattie et al., 2002, *Science* 295, 2282-2285); disruption of these functions could impair the function of the nervous system and lead to neurodegeneration. Finally, there are indications that astrocytes may serve as immune effector cells in the brain (Dong & Benveniste, 2001, *Genomics* 33, 292-297); disruption of this function could weaken immune responses against HIV-1, particularly the recruitment of macrophages into the brain (Lipton & Gendelman, 1995, *New Engl. J. Med.* 233, 934-940).

The AEGs (Table 1) and ASGs (Table 2) identified thus far can provide leads for investigation of cellular pathways co-opted by HIV-1 in astrocytes. One important indicator is the time of gene activation or suppression relative to HIV-1 infection. Early modulation of cellular genes (6 h and 24 h after Hw-1 infection in our studies) may indicate direct cellular responses to HIV-1 mediated by signal transduction mechanisms activated by virus interaction with cell surface receptors or by disruption of the plasma membrane integrity during virus-cell fusion. Such responses were observed after HIV-1 exposure in T cells (Gupta & Vayuvegula, 1987, *J. Clin Immun* 7, 486-489; Fermin & Garry, 1992, *Virology* 191, 941-946; Miller et al., 1993, *Virology* 196, 89-100), macrophages (Zheng et al., 1999, *J. Virol* 73, 8256-8267; Choe et al., 2001, *J. Virol* 75, 10738-10745), and neurons (Zheng et al., 1999, *J. Virol* 73, 8256-8267). The early-responder genes are represented by ASG-4, -7, and -8, all of which show a decline in expression within 6-24 h after HIV-1 infection (FIG. 12). ASG-4 is of particular interest in the context of HIV-1 infection. This gene codes for C3G, a guanine nucleotide releasing (exchange) protein that was originally identified as one of the two major proteins binding to the Src homology-3 (SH3) domain of the Crk adaptor protein (Tanaka et al., 1994, *Proc. Natl. Acad. Sci. USA* 91, 3443-3447). The Crk-C3G complex transduces signals from tyrosine-phosphorylated receptors (RTKs) in the plasma membrane to Rap1, a member of Ras-family G-proteins (York et al., 1998, *Nature* 392, 622-626), and subsequently to Jun kinase, JNK (Tanaka et al., 1997, *Science* 276, 1699-1702). The exact role of the RTK/Crk/C3G/Rap1 signaling pathway has not been fully characterized (Tanaka et al., 1997, *Science* 276, 1699-1702), but published data indicate that it may exert pluripotent effects on cellular gene expression, possibly depending on the initiating signal. For example, Rap1 was shown to antagonize Ras-mediated cell transformation and MAP kinase activation in Rat-1 fibroblasts and cloned rat embryo fibroblasts (CREF), (Cook et al., 1993, *EMBO J.* 12, 3475-3485; Su et al., 1993, *Oncogene* 8, 1211-1219) but, conversely, it mediated sustained MAP kinase activation and cell differentiation in response to NGF in PC12 cells (York et al., 1998, *Nature* 392, 622-626) and C3G-dependent Rapi activation promoted adhesion of mouse embryonic fibroblasts (Ohba et al., 2001, *EMBO J.* 20, 3333-3341). Of note, the Crk/C3G pathway was recently shown to serve as a downstream effector for the latency-associated protein LMP2A of Epstein-Barr virus, a major human pathogen (Engels et al., 2001, *J. Exp. Med.* 194, 255-264). The observed downregulation of C3G in astrocytes by HIV-1 may thus disrupt an important cellular signaling pathway and the functions it controls including, if cell adhesion is affected (Ohba et al., 2001, *EMBO J.* 20, 3333-3341), the activity of astrocytes as antigen-presenting cells (Dong & Benveniste, 2001, *Genomics* 33, 292-297). Of the other two early-response genes in HIV-1 infected astrocytes, ASG-8 is a homolog of the *Drosophila* trithorax gene and ASG-7 is a partially characterized transcription regulation factor that belongs to the zinc finger protein family (Liebhaber et al. 1990, Nucleic Acids Res 18, 3871-3879). Sequence analysis of ASG-8 suggests that it contains four putative zinc fingers, which may have evolved by duplication of a preexisting two-finger unit (Liebhaber et al. 1990, Nucleic Acids Res 18, 3871-3879). This human cysteine-rich protein gene is highly conserved and was detected in every nucleated tissue and cell line tested (Liebhaber et al. 1990, Nucleic Acids Res 18, 3871-3879). Although further experimentation is necessary, changes in expression of this transcription factor could affect expression of target genes in astrocytes that may contribute to normal astrocyte physiology.

Similar to the AEG series of astrocyte genes, the majority of ASGs described here (6 out of 10) appear to be late-response genes, that is, their expression declined maximally only 3 d to 7 d after HIV-1 infection. These genes include ASG-1 (novel), ASG-3 (platelet-endothelial cell tetra-span antigen 3, or CD 151 /PETA-3; Fitter et al., 1995, *Blood* 86, 1348-55; Yáñez-Mó et al., 1998, *J. Cell Biol.* 141, 791-804), ASG-5 (neuronatin; Dou & Joseph, 1996, *Brain Res.* 723, 8-22; Usui et al., 1997, *J. Mol. Neurosci.* 9, 55-60), ASG-6 (neuroendocrine differentiation factor; CGI149; Wilson et al., 2001, *J. Clin. EndocrinoL Metab.* 86, 4504-11), ASG-9 (human mitochondrion genomic DNA, this fragment is homologous to the 952 to 1232-bp region of genomic DNA which encodes 16s rRNA (from the 650 to 1603-bp region of genomic DNA), and ASG-10 (signal recognition particle, SRP9; Lütcke, 1995, *Eur. J. Biochem.* 228, 531-550). PETA-3 (ASG-3) is a glycoprotein of 253 amino acids that belongs to the tetraspanin family of surface proteins (Fitter et al., 1995, *Blood* 86, 1348-55; Testa et al., 1999, *Cancer Res* 59, 3812-3820). PETA-3 RNA is downmodulated almost 4-fold in infected versus uninfected astrocytes (Table 2). Although PETA-3 was originally identified as a platelet surface protein, recent data indicate that it functions as a component of integrin signaling complexes on endothelial cells and it may be involved in regulation of cell motility (Yáñez-Mó et al., 1998, *J. Cell Biol.* 141, 791-804; Testa et al, 1999, *Cancer Res* 59, 3812-3820). Downmodulation of PETA-3 in astrocytes by HIV-1 may affect astrocyte function in maintaining the integrity of the blood-brain-barrier (BBB) by reducing both the flexibility and adhesion strength of the astrocytic underlayer of the BBB (Morgello et al., 1995, *Glia* 14, 43-54). Neuronatin (ASG-5) is a brain-specific human protein that is selectively expressed during development (Dou & Joseph, 1996, *Genomics* 33, 292-297; Dou & Joseph, 1996, *Brain Res.* 723, 8-22) and therefore it is unlikely to play a role in the adult disease such as HAD. The five-fold downmodulation of neuronatin observed here is of interest because of the proposed function of the protein as a regulator of anion channels (Dou & Joseph, 1996, *Brain Res.* 723, 8-22), an activity that may be functionally related to the observed downregulation of glutamate transport in these cells (Wang et al., 2002, *J. Virol.*, in press).

The neuroendocrine differentiation factor, NEDF (ASG-6), has been recently identified by a yeast two-hybrid screening as a novel intracellular protein that interacts with the IGF-binding protein-related protein-1 (IGFBP-rP1) and proposed to act together with IGFBP-rP1 in inducing neuroendocrine cell differentiation in response to IGF (Wilson et al., 2001, *J. Clin. Endocrinol. Metab.* 86, 4504-11). ASG-6 is of interest in the context of HIV-1 infection because IGF-like growth factors appear to be protective during CNS injury (Bondy & Lee, 1993, *Ann. N.Y. Acad. Sci.* 692, 33-43) and HIV-1 disease correlates with defects in the insulin-like growth factor system (Frost et al., 1996, *Clin. Endocrinol.* 44, 501-514; Jain et al., 1998, *Endocr. Rev.* 5, 625-646). Also of note, it has been suggested that the NEDF (ASG-6)/IGFBP-rP1 complex acts through the Ras/MAPK signaling pathway (Wilson et al., 2001, *J. Clin. Endocrinol. Metab.* 86, 4504-11), an alternative to the Crk/C3G/Rap1 pathway discussed earlier in the context of observed downmodulation of C3G (ASG-4). Thus two genes in astrocytes whose expression is reduced by HIV-1, one early (ASG-4) and one late (ASG-6) after infection, encode products that transduce signals from RTKs, indicating that this signal transduction pathway is a major target for HIV-1 mediated dysregulation of astrocyte physiology. Experiments are now under way to investigate this possibility.

ASG-10 encodes a signal recognition particle SRP9, a component of Alu RNA binding heterodimer SRP9/14 (Lütcke, 1995, *Eur. J. Biochem.* 228, 531-550). SRP targets secretory and membrane proteins to rough endoplasmic reticulum in a complex, co-translational process that includes a temporary arrest of elongation (Lütcke, 1995, *Eur. J. Biochem.* 228, 531-550). In the CNS, the heterodimer SRP9/14 was found to be an integral part of the brain-specific BC200 RNA, a small non-messenger RNA that is a constituent of a ribonucleoprotein complex in neurons and that is believed to regulate protein biosynthesis in dendrites (Kremerskothen et al., 1998, *Neurosci. Lett.* 245, 123-126). Downmodulation of SRP9 expression by HIV-1 may impair the formation and function of the SRP9/14 heterodimer and, consequently, affect synthesis of secretory and membrane proteins by astrocytes. The virus could adopt this mechanism as a means for reducing exposure of infected astrocytes to immune recognition, similar in an outcome to the Nef-mediated downmodulation of HLA-Class I in T lymphocytes (Collins et al., 1998, *Nature* 391, 397-401).

Various publications are cited herein, the contents of which are hereby incorporated by reference in their entireties.

What is claimed is:

1. An isolated nucleic acid molecule, the sequence of which comprises nucleotides 220-1968 of SEQ ID NO:1.

2. The nucleic acid molecule of claim 1, operably linked to a promoter element.

3. The nucleic acid molecule of claim 2, as comprised in a vector.

4. A cell culture comprising cells containing the isolated nucleic acid of claim 1 operably linked to a heterologous promoter.

5. The cell culture of claim 4, wherein said cells are astrocytes.

6. An isolated nucleic acid molecule encoding a protein, the sequence of which comprises SEQ ID NO: 2.

7. An isolated nucleic acid molecule comprising residues which are at least 90 percent identical to nucleotides 220-1968 of SEQ ID NO:1.

* * * * *

SEQUENCE LISTING

<160> NUMBER OF SEQ ID NOS: 7

<210> SEQ ID NO 1
<211> LENGTH: 3611
<212> TYPE: DNA
<213> ORGANISM: Homo sapiens

<400> SEQUENCE: 1

```
tcctggcggc ggcggagtga ggctgacagc ggggaacctg ggagacccct ccgccctccc      60
cgcggtggca gcggccgatc cccggctccg gcgcgaggga cggccgcgat gcgctcggcc     120
tgaggttacc cggcccggcc cttcctcgct tccctcgact attccactgc gtctccgcgc     180
cccggcgtca tcctgcgagt ccctctgacg ggagggaaga tggctgcacg gagctggcag     240
gacgagctgg cccagcaggc cgaggagggc tcggcccggc tgcgggaaat gctctcggtc     300
ggcctaggct ttctgcgcac cgagctgggc ctcgacctgg ggctggagcc gaaacggtac     360
cccggctggg tgatcctggt gggcactggc gcgctcgggc tgctgctgct gtttctgctg     420
ggctacggct gggccgcggc ttgcgccggc gcccgcaaaa agcggaggag cccgccccgc     480
aagcgggagg aggcggcggc cgtgccggcc gcggcccccg acgacctggc cttgctgaag     540
aatctccgga gcgaggaaca gaagaagaag aaccggaaga aactgtccga gaagcccaaa     600
ccaaatgggc ggactgttga agtggctgag ggtgaagctg ttcgaacacc tcaaagtgta     660
acagcaaagc agccaccaga gattgacaag aaaaatgaaa agtcaaagaa aaataagaag     720
aaatcaaagt cagatgctaa agcagtgcaa aacagttcac gccatgatgg aaaggaagtt     780
gatgaaggag cctgggaaac taaaattagt cacagagaga aacgacagca gcgtaaacgt     840
gataaggtgc tgactgattc tggttcattg gattcaacta tccctgggat agaaaatacc     900
atcacagtta ccaccgagca acttacaacc gcatcatttc ctgttggttc caagaagaat     960
aaaggtgatt ctcatctaaa tgttcaagtt agcaacttta aatctggaaa aggagattct    1020
acacttcagg tttcttcagg attgaatgaa aacctcactg tcaatggagg aggctggaat    1080
gaaaagtctg taaaactctc ctcacagatc agtgcaggtg aggagaagtg gaactccgtt    1140
```

```
tcacctgctt ctgcaggaaa gaggaaaact gagccatctg cctggagtca agacactgga      1200
gatgctaata caaatggaaa agactgggga aggagttgga gtgaccgttc aatattttct      1260
ggcattgggt ctactgctga gccagtttct cagtctacca cttctgatta tcagtgggat      1320
gttagccgta atcaacccta tatcgatgat gaatggtctg ggttaaatgg tctgtcttct      1380
gctgatccca actctgattg gaatgcacca gcagaagagt ggggcaattg ggtagacgaa      1440
gaaagagctt cacttctaaa gtcccaggaa ccaattcctg atgatcaaaa ggtctcagat      1500
gatgataaag aaaagggaga gggagctctt ccaactggga atccaaaaa gaaaaaaaag      1560 aaaagaaga agcaaggtga agataactct actgcacagg acacagaaga attagaaaaa      1620
gagattagag aagaccttcc agtgaatacc tctaaaaccc gtccaaaaca ggaaaaagct      1680
ttttccttga agaccataag cactagtgat ccagccgaag tactcgtcaa aaatagccag      1740
cctatcaaga ctcttccacc tgctacttct accgagccat ctgtaatctt atcaaaaagt      1800
gattctgaca agagctcttc ccaagtgccg ccaatactac aagagacaga taaatccaag      1860
tcaaatacca agcaaaatag tgtgcctcct tcacagacca agtctgaaac tagctgggaa      1920
tctcccaaac aaataaaaaa gaagaaaaaa gccagacgag aaacgtgaaa ttttttttcc      1980
tgaattggac atgtgtttgc aaacacttgt cttgaagatt atgctgttta tgcaataatt      2040
tgtgaacatg tacagagttt tatataaatt taaaccaatt tttaaaacaa aactgcggac      2100
accaccataa aaatggaatc aaaagaaagt taatttatga aattaagagg tcagcagaat      2160
atactcagtg atggaagaca cttgggaaag tcttttttaat agaacaagaa cgatcttaat      2220
ttaagaatat tatcctggtt taacaacagt gccctgttta caacagattg tgccctatct      2280
catctgcagc cgaggaataa aggattctga ttagaaagag ggttgcctac agattagtaa      2340
gcaattcctt ggatcttatg cacagaactt gtaccatttg aatctgtttt atgcttaaat      2400
caaagtgctt tgatcaaatg cataacctgc catatcttta catatttgtt ggtagcaatt      2460
tgtattaaag aaatcacaag tgcaaataaa aagtcattta tcatttgttt aactaaactg      2520
tcatggttta gtttacaatt tttaaaaagt tcttaaaata ctgaaaatgc agttgacact      2580
tgtgtatggc ttatgaagtt attttttgata gtcttacatt acttgaattg ttcaaagtac      2640
agtatatttt aaattaagaa aagtgaacta tatgtatttg ttttatacat ttaaggctta      2700
gactcataaa taatgctatt gtttatgatt tgaaaacttt caggcaaaat ccaatttaca      2760
tttttccctt ccctagcaat tactttttc cagcttcaac tcttcttagt tactaatact      2820
ttgttgactt taaaaatgaa atcattcaca aacttttggt atatgatgga gaatgaaaaa      2880
ctagagtcag acagctttaa ttgacattgt caacacctcc agttatcagg aatacatttt      2940
tttactgcct taacctgtag tgcgtagaat atgcatcaat ttcttgaagg agattcatgt      3000
ttttataaga attttcatgt aattattgca attgtggtca aataaggaac gtttcctgct      3060
tgaaattata ttgatttaaa tgatgtgtga gatgtttcac cattttcagg cactgtgtaa      3120
ttctattgta ataaactggc aggtatcttt gtaactataa atagtgcatg ctcagccatg      3180
tacactgtaa atagccttta ccaaacgtgt ttgacaagga ccataattaa catcacttag      3240
tgaattgtga taaagaaaaa aaagccatga tttattcgat gtgattggct tgttttttatg      3300 tggcgccaag aacgaacctg tttaacagct gtaaccaatg gtactgatct atccatccaa      3360
tgttgtcatt atatttgact gtggttcaac agtattgcgt tgtcagacta ggaaagctaa      3420
acgaacaaaa tggtttttagt tttgctgaag actggcctta ttaatggaca gctttcctaa      3480
```

```
caagagatta ttaactttta tcaggtgtta acatctgttt caggaacatg gcagtatgtt    3540
tacatgtcag aagttttgtt taattctatg gtatttctaa attgacttgt ttaaataaat    3600
tcagcaaatg g                                                        3611
```

<210> SEQ ID NO 2
<211> LENGTH: 582
<212> TYPE: PRT
<213> ORGANISM: Homo sapiens

<400> SEQUENCE: 2

```
Met Ala Ala Arg Ser Trp Gln Asp Glu Leu Ala Gln Gln Ala Glu Glu
 1               5                  10                  15

Gly Ser Ala Arg Leu Arg Glu Met Leu Ser Val Gly Leu Gly Phe Leu
            20                  25                  30

Arg Thr Glu Leu Gly Leu Asp Leu Gly Leu Glu Pro Lys Arg Tyr Pro
        35                  40                  45

Gly Trp Val Ile Leu Val Gly Thr Gly Ala Leu Gly Leu Leu Leu Leu
    50                  55                  60

Phe Leu Leu Gly Tyr Gly Trp Ala Ala Ala Cys Ala Gly Ala Arg Lys
65                  70                  75                  80

Lys Arg Arg Ser Pro Pro Arg Lys Arg Glu Glu Ala Ala Ala Val Pro
                85                  90                  95

Ala Ala Ala Pro Asp Asp Leu Ala Leu Leu Lys Asn Leu Arg Ser Glu
            100                 105                 110

Glu Gln Lys Lys Lys Asn Arg Lys Lys Leu Ser Glu Lys Pro Lys Pro
        115                 120                 125

Asn Gly Arg Thr Val Glu Val Ala Glu Gly Glu Ala Val Arg Thr Pro
    130                 135                 140

Gln Ser Val Thr Ala Lys Gln Pro Pro Glu Ile Asp Lys Lys Asn Glu
145                 150                 155                 160

Lys Ser Lys Lys Asn Lys Lys Ser Lys Ser Asp Ala Lys Ala Val
                165                 170                 175

Gln Asn Ser Ser Arg His Asp Gly Lys Glu Val Asp Glu Gly Ala Trp
            180                 185                 190

Glu Thr Lys Ile Ser His Arg Glu Lys Arg Gln Gln Arg Lys Arg Asp
        195                 200                 205

Lys Val Leu Thr Asp Ser Gly Ser Leu Asp Ser Thr Ile Pro Gly Ile
    210                 215                 220

Glu Asn Thr Ile Thr Val Thr Glu Gln Leu Thr Thr Ala Ser Phe
225                 230                 235                 240

Pro Val Gly Ser Lys Lys Asn Lys Gly Asp Ser His Leu Asn Val Gln
                245                 250                 255

Val Ser Asn Phe Lys Ser Gly Lys Gly Asp Ser Thr Leu Gln Val Ser
            260                 265                 270

Ser Gly Leu Asn Glu Asn Leu Thr Val Asn Gly Gly Trp Asn Glu
        275                 280                 285

Lys Ser Val Lys Leu Ser Ser Gln Ile Ser Ala Gly Glu Glu Lys Trp
    290                 295                 300

Asn Ser Val Ser Pro Ala Ser Ala Gly Lys Arg Lys Thr Glu Pro Ser
305                 310                 315                 320

Ala Trp Ser Gln Asp Thr Gly Asp Ala Asn Thr Asn Gly Lys Asp Trp
                325                 330                 335

Gly Arg Ser Trp Ser Asp Arg Ser Ile Phe Ser Gly Ile Gly Ser Thr
            340                 345                 350
```

```
Ala Glu Pro Val Ser Gln Ser Thr Thr Ser Asp Tyr Gln Trp Asp Val
        355                 360                 365

Ser Arg Asn Gln Pro Tyr Ile Asp Asp Glu Trp Ser Gly Leu Asn Gly
    370                 375                 380

Leu Ser Ser Ala Asp Pro Asn Ser Asp Trp Asn Ala Pro Ala Glu Glu
385                 390                 395                 400

Trp Gly Asn Trp Val Asp Glu Glu Arg Ala Ser Leu Leu Lys Ser Gln
                405                 410                 415

Glu Pro Ile Pro Asp Asp Gln Lys Val Ser Asp Asp Lys Glu Lys
            420                 425                 430

Gly Glu Gly Ala Leu Pro Thr Gly Lys Ser Lys Lys Lys Lys Lys
        435                 440                 445

Lys Lys Lys Gln Gly Glu Asp Asn Ser Thr Ala Gln Asp Thr Glu Glu
    450                 455                 460

Leu Glu Lys Glu Ile Arg Glu Asp Leu Pro Val Asn Thr Ser Lys Thr
465                 470                 475                 480

Arg Pro Lys Gln Glu Lys Ala Phe Ser Leu Lys Thr Ile Ser Thr Ser
                485                 490                 495

Asp Pro Ala Glu Val Leu Val Lys Asn Ser Gln Pro Ile Lys Thr Leu
            500                 505                 510

Pro Pro Ala Thr Ser Thr Glu Pro Ser Val Ile Leu Ser Lys Ser Asp
        515                 520                 525

Ser Asp Lys Ser Ser Ser Gln Val Pro Pro Ile Leu Gln Glu Thr Asp
    530                 535                 540

Lys Ser Lys Ser Asn Thr Lys Gln Asn Ser Val Pro Pro Ser Gln Thr
545                 550                 555                 560

Lys Ser Glu Thr Ser Trp Glu Ser Pro Lys Gln Ile Lys Lys Lys Lys
                565                 570                 575

Lys Ala Arg Arg Glu Thr
            580

<210> SEQ ID NO 3
<211> LENGTH: 1594
<212> TYPE: DNA
<213> ORGANISM: Homo sapiens
<220> FEATURE:
<221> NAME/KEY: misc_feature
<222> LOCATION: 115
<223> OTHER INFORMATION: n = A,T,C or G

<400> SEQUENCE: 3
gcggaaataa acaaaatgag tagacatggg aacataaaat acattgtgga atatccaagt      60
aataatgcat tatgacatta tctaatgttt ctgaagaaca tatattatca agggnaatgg    120
ccgcattctt ttcatgccca tggcagacag agcaaaccta aatgtgcaag catatatcaa    180
gcttctgtag agtcaggttt ctcaaattat cattgaccaa aataagttac atggccaagg    240
ccaagctcta catcaataat caggaaacag ctgggtgcag tggctcacac tatttttcata   300 ttattagtat taaaattccc atttgcatat ggttatagat ttcttaccaa cttccatatt    360
ttcaaactga aaaaatgtaa aactaaattc ttttttagaa actccatgtg tgataaataa    420
aattatttaa catttggtg taatatttac aaatcctgca aaatagcacc cagatccttg     480
gttgatgcca gagtcactct gcattatgca atgacacttt aggcaaaaag taataataat    540
agctgcaaag aaacattcaa gaatactgta ctaaatgcaa ctaaactcta caataaatgc    600
aaagtatcag cacttaagtg gattagttga agtgtgccat tatcatgcca gggtgacata    660
```

-continued

```
acacaacaca atggcatata ccattgtatc agagtagagg aaacctttct ctccttttca      720
catttgcata tggttacgtt taaattacca cctatttat ataataactg gcaggtgtta       780
tgataaagat attaaataac attccatttt ttcattaaag aaatcaaaat atagaatagc      840
cctaaagaaa ctgagagttg tgtacaggtt ttatgagcac agaagcactt ttaaatatgt      900
aacaggggac atgcaaacat tggaacatca gaattagcca ccgtaattct ctaatctcca     960
tgtttctatt tgtatataat ctgaaacagg gaaactatac tcacaatcag ggaaaactac     1020
tggtaaattg ttcatgccat tgcataataa aatggctaaa gtagttaaaa agtaatgaat     1080
ctggaagtct ttagcagaca tattcagtgt aacttatgtc acacttaaaa gagaaaaata    1140 gtattaaaaaa ttagagatct tttatcttcc cttagtaaat aacctttct atcgaaacaa    1200 aattacttga gtctaaatcc tgttataagc acagtgttag atatcttaca tatattattt    1260
cattgaatac taacaaaaaa ccctttgata aacatggtat tcttcccagt ttatagagat    1320
ggaaacatag aaattaggta atgtgcccat gtttgtacag gtaataagtg gtagacctgg    1380
atctaaaata catattaggc ttcaaactaa ttcatactct aaaagaatat ttgccaaagt    1440
acataataca atttgctaac agatgctaag gtaaacaaaa aattgattat gatagttaat   1500
ttacacaagg ataagttata agctaaaata ttttttttccc ttaacaaaat attatgtatc   1560
atttatttat ttatttttt gaaacggagt ctcg                                 1594
```

<210> SEQ ID NO 4
<211> LENGTH: 2720
<212> TYPE: DNA
<213> ORGANISM: Homo sapiens

<400> SEQUENCE: 4

```
gagagctctc attttccccc cttgctcggg atggtgccac aggaggctgt gcgggccccg       60
ctccgcttcg aatggttgtg ttgatgttcc tttcagctgg tcctatagta cccctcctca     120
ggaatgtctc cccagtgcaa ggacaaagac tgaagagact gctatattga tggactctca    180
agccaactat gaagttgaaa caagaaagt gatcacctga agacacctcc tctgctaaga     240
aacaccccca aattgtgcag cttctgccac tagaactctc agaacaagag acaatctttt    300
caagaaacag aaaaactcaa taatgacatc tagattttca tgagccaaga actttcccctt   360 cctcatgtgt attcctctgt ttgtacttaa attcatgtga cattcatttt tttcctagta    420
tggatatgct tattaatgca cttgtttcaa aatcccaaat tgcacaaatg tgttaatatt    480
ttaagaaaca aaatgaatcc tacaaggaga atgattttta gccacacata gggttggatc    540
ttgagagtga cctacagaat aaaagtactt ttaaaataaa gtagtcagag gctattcaaa    600
gggtaaaata atcatagtac cacattggtc cacttgacac taaccaatcg atcatttttt    660
tttaatcaag aaagctagat tctatcagat aaaatcactg cttctaaaga gtttaaatct    720
agttagaaaa agttatagaa atgtttgcaa agataagtaa cagatagagt cagtagagga    780
taagatcaaa aacaaaacca agcaaaagat gagttcaggg gagtttgcca tcaagttggc    840
aaaactgact tacttaggga agaaagttat aaaacaggaa aatatgagat gaaccttgag    900
tgatgtggaa gatttagata atggaaagg aaggagaaaa tggagttctt taggtggttg     960
taattggagg aggaaatgaa tacacacatc ttgttgactt aaacccagac attcagcagc    1020
tctctataca tatctggaaa agactgcaca gtcacctcct gtctctcacc ccaggtatta    1080
cttagaatta ttatcatatt tcccttcctt taaagtaagt aagggtgatt ggtgacaata    1140
```

```
tggagaacta tgattttcc attaacctaa taataattgg tatttattga gttctgttaa    1200
gcattttaca tattaactca cttaagccctt tcaacagcct tgcaaaatag gtattattat    1260
ccccatttta caggcaagaa aactgaggtt taagtaactt gccgaagtgc catatacagg    1320
gctcacattc agtattgcag ttgcaaagct catgatctat agtgccaagt tgcaatattg    1380
tagtcaatgt cacaattatt acccctttt atattccttg atattttcc atggcaaaca    1440 attagctatt tcatttaata atcacctaaa acttttcagt cttctgatta aaattacgct    1500
ggagtgatag aatgtatttt catgatagaa attgggaaaa aaatgggga atgaagttta    1560 tcagcatttc agacttgttt ttttttttt tttttgcaa gactttgatg agattgttca    1620
cttttgtcta tgtaaaatcc caaatccttg agaataaaaa aggggaggt ttaagtcact    1680 tgttgcaatg ccctttttaa tagaggcaat aaatctaaag gccataaatt tagagtgact    1740
tacagaagat cgaactttgg agtgtggcag agtaagggat ggaaaccggg ccctccagtt    1800
cactatcagt agcttttgca ctggtctgcc cttcctaaat taagtatgca cttcaatttg    1860
atgagtggaa acagtctatc tgggcagtaa ccagggagct ttgtgcctag tagattgctt    1920
ctgttctgca cttctttggt ttcccacctc aatgtaaaaa atagctagca atgaagtcca    1980
gaagttgtca atggttcatc cccagaagaa tgcataatgt ccaaagttgt atgtgtatga    2040
tgtcttcaat ggtattaagt tatttcaaat tcttagttca cctacataaa tcatttctaa    2100
caagcatctt cttaaccaac tttatgcaca gtgtatgttt gtaagtgctt ctgcacgaat    2160
gtttatacat gactgtttcc atagtactta tgttttaaa aatattcagt catttcctac    2220
tataatcctc atgtatccat gtaactgact caaaaatact tcagccacag aaagctaaaa    2280
ctgagcaaat ctcattcttc ttttccatcc cctttgcatg tggctggcat ttagtaatga    2340
ttaataatat ggccagctga ataacagagg tttgagacac aattctttct caaaggagtc    2400
agctaagctg ggtctactta tggacaaaca tctaaatgtg tggaagtatc tgatatttga    2460
caatggtaaa tttccactta gctagctagc attgtcagac ttcaatctcc tcatggctct    2520
ggccgtcctg ttttaagcat gataattgtt ggccacatct cacatagttc tcattgagtg    2580
agttcataaa taaacagggt ttttttttt tttaaagagc agccaagcac aaagtgtgac    2640
tttgttgaca ttttatgtga ctttgtcata tgttcctaac ccccaataaa agcaatgttg    2700
caccaaaaaa aaaaaaaaaa                                                2720

<210> SEQ ID NO 5
<211> LENGTH: 18
<212> TYPE: DNA
<213> ORGANISM: Homo sapiens

<400> SEQUENCE: 5
ctgatcactc gagagatc                                                    18

<210> SEQ ID NO 6
<211> LENGTH: 14
<212> TYPE: DNA
<213> ORGANISM: Homo sapiens

<400> SEQUENCE: 6
ctgatcactc gaga                                                        14

<210> SEQ ID NO 7
<211> LENGTH: 12
<212> TYPE: DNA
<213> ORGANISM: Homo sapiens
```

```
<400> SEQUENCE: 7
gatctctcga gt                                                          12
```